US010851039B2

(12) United States Patent
Nakamura et al.

(10) Patent No.: US 10,851,039 B2
(45) Date of Patent: Dec. 1, 2020

(54) POLYHYDRIC PHENOL COMPOUND AND METHOD OF PRODUCING SAME

(71) Applicant: MITSUBISHI CHEMICAL CORPORATION, Chiyoda-ku (JP)

(72) Inventors: Takeshi Nakamura, Chiyoda-ku (JP); Yoshie Takami, Chiyoda-ku (JP); Tomoko Maeda, Chiyoda-ku (JP); Naoko Sumitani, Chiyoda-ku (JP); Hiroki Shibata, Chiyoda-ku (JP); Toshiki Monden, Chiyoda-ku (JP)

(73) Assignee: MITSUBISHI CHEMICAL CORPORATION, Chiyoda-ku (JP)

( * ) Notice: Subject to any disclaimer, the term of this patent is extended or adjusted under 35 U.S.C. 154(b) by 0 days.

(21) Appl. No.: 16/352,471

(22) Filed: Mar. 13, 2019

(65) Prior Publication Data

US 2019/0210947 A1 Jul. 11, 2019

Related U.S. Application Data

(63) Continuation of application No. PCT/JP2017/033096, filed on Sep. 13, 2017.

(30) Foreign Application Priority Data

Sep. 14, 2016 (JP) .................................. 2016-179770
Jun. 12, 2017 (JP) .................................. 2017-115240

(51) Int. Cl.
| C07C 39/16 | (2006.01) |
| C07C 37/20 | (2006.01) |
| C08G 64/06 | (2006.01) |
| C08G 59/06 | (2006.01) |
| C07C 37/84 | (2006.01) |
| C07C 37/88 | (2006.01) |
| G03C 7/413 | (2006.01) |
| C07C 37/68 | (2006.01) |

(52) U.S. Cl.
CPC .............. *C07C 39/16* (2013.01); *C07C 37/20* (2013.01); *C07C 37/84* (2013.01); *C07C 37/88* (2013.01); *C08G 59/06* (2013.01); *C08G 64/06* (2013.01); *G03C 7/413* (2013.01); *C07C 37/68* (2013.01)

(58) Field of Classification Search
None
See application file for complete search history.

(56) References Cited

U.S. PATENT DOCUMENTS

| 4,260,831 A | 4/1981 | Matsushima et al. |
| 4,446,285 A | 5/1984 | Mark et al. |
| 4,469,861 A | 9/1984 | Mark et al. |
| 4,547,564 A | 10/1985 | Mark et al. |
| 6,465,697 B1 | 10/2002 | Palmer et al. |

| 2002/0102502 A1 | 8/2002 | Fukui et al. |
| 2004/0053174 A1 | 3/2004 | Fukui |
| 2004/0101794 A1 | 5/2004 | Usagawa et al. |

FOREIGN PATENT DOCUMENTS

| CN | 1133855 A | 10/1996 |
| CN | 1466605 A | 1/2004 |
| CN | 102459139 A | 5/2012 |

(Continued)

OTHER PUBLICATIONS

International Search Report dated Oct. 10, 2017 in PCT/JP2017/033096 filed Sep. 13, 2017.
Shono, T., et al., "Reaction of Higher Aliphatic Aldehydes", Journal of the Chemical Society of Japan, vol. 59, Issue 8, 1956, pp. 960-962 (with English Translation).
International Preliminary Report on Patentability and Written Opinion dated Mar. 28, 2019 in PCT/JP2017/033096 (submitting English translation only), 7 pages.

(Continued)

*Primary Examiner* — Ana Z Muresan
(74) *Attorney, Agent, or Firm* — Oblon, McClelland, Maier & Neustadt, L.L.P.

(57) ABSTRACT

The present invention provides a polyhydric phenol compound which has an excellent alkali resistance and which does not cause a deterioration in color even when used as a resin raw material or a color developer. The polyhydric phenol compound includes: a bisphenol compound (A) represented by the following Formula (1) and a trisphenol compound (B) represented by the following Formula (2):

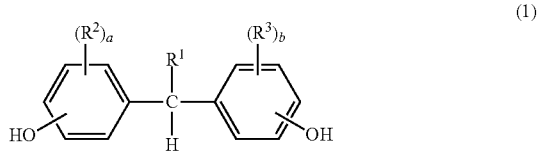

(1)

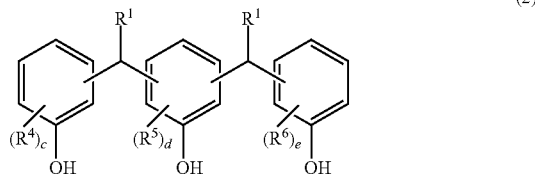

(2)

[wherein $R^1$ represents a monovalent aliphatic hydrocarbon group having from 6 to 24 carbon atoms; each of $R^2$, $R^3$, $R^4$, $R^5$ and $R^6$ represents a monovalent hydrocarbon group having from 1 to 15 carbon atoms; and each of a, b, c, d and e represents an integer from 0 to 4];

wherein the trisphenol compound (B) is contained in an amount, in terms of absorption intensity ratio at 254 nm, of less than 1.6% by area with respect to the amount of the bisphenol compound (A).

3 Claims, No Drawings

(56) References Cited

FOREIGN PATENT DOCUMENTS

| | | |
|---|---|---|
| CN | 101448772 B | 10/2012 |
| CN | 105085192 A | 11/2015 |
| EP | 0 112 530 A2 | 7/1984 |
| JP | S49-48319 B1 | 12/1974 |
| JP | 53-116357 | 10/1978 |
| JP | 59-131623 | 7/1984 |
| JP | 59-167528 | 9/1984 |
| JP | S63-170417 A | 7/1988 |
| JP | 8-208546 A | 8/1996 |
| JP | 8-245465 | 9/1996 |
| JP | 9-301911 | 11/1997 |
| JP | 2000-43412 | 2/2000 |
| JP | 2002-169249 | 6/2002 |
| JP | 2004-145201 | 5/2004 |
| JP | 3527785 B2 | 5/2004 |
| JP | 2011-80025 | 4/2011 |
| JP | 2015-212245 | 11/2015 |
| TW | 201542619 A | 11/2015 |
| WO | WO 00/35847 A1 | 6/2000 |

OTHER PUBLICATIONS

Extended European Search Report dated Jul. 10. 2019 in European Patent Application No. 17850935.2, citing documents AO, AP and AQ therein. 7 pages.

Shono, T., et al., "Reaction of Higher Aliphatic Aldehydes", Journal of the Chemical Society of Japan, vol. 59, Issue 8, 1956, 10 pages (with English Translation).

Office Action dated Sep. 18, 2020 and Search Report issued in corresponding Chinese application No. 201780055902.7 w/Machine Translation.

POLYHYDRIC PHENOL COMPOUND AND METHOD OF PRODUCING SAME

CROSS-REFERENCE TO RELATED APPLICATION

This is a continuation of International Application PCT/JP2017/033096, filed on Sep. 13, 2017, and designated the U.S., and claims priority from Japanese Patent Application 2016-179770 which was filed on Sep. 14, 2016, and Japanese Patent Application 2017-115240 which was filed on Jun. 12, 2017, the entire contents of which are incorporated herein by reference.

TECHNICAL FIELD

The present invention relates to a polyhydric phenol compound and a method of producing the same. More particularly, the present invention relates to: a polyhydric phenol compound which contains a specific bisphenol compound having a molecular structure in which a long chain alkyl residue is present between two aromatic nuclei each having a phenolic hydroxyl group, and a trisphenol compound having a specific structure, at a specific ratio; and a method of producing the same.

The polyhydric phenol compound according to the present invention is useful as: a raw material for producing a resin such as a polycarbonate resin or an epoxy resin; a curing agent, a color developer or an anti-fading agent; or any other additive such as a bactericide, an antibacterial antifungal agent or the like.

Further, the present invention relates to a resin produced using the polyhydric phenol compound according to the present invention, such as a polycarbonate resin, and to a method of producing the same.

BACKGROUND ART

Polyhydric phenol compounds containing bisphenol compounds as major components have conventionally been used widely and usefully as: raw materials for thermoplastic resins such as polycarbonate resins, polyarylate resins and acrylate resins; raw materials for thermosetting resins such as epoxy resins and polyimide resins; curing agents; as well as color developers and anti-fading agents for thermosensitive recording; and other additives such as antioxidants, bactericides, antibacterial antifungal agents and flame retardants; and are increasing in their importance.

Among such polyhydric phenol compounds, Non-patent Document 1 discloses a polyhydric phenol compound which contains a long chain alkyl group and which is produced by allowing nonyl aldehyde to react with phenol. Further, Patent Document 1 also discloses a rubbery polycarbonate obtained using as a raw material, a polyhydric phenol compound which contains a long chain alkyl group and which is produced by allowing a long chain aliphatic aldehyde to react with phenol, in a similar manner as with the above compound.

Since such a polyhydric phenol compound containing a long chain alkyl group includes a soft segment derived from the long chain alkyl group within the molecular skeleton, the use of such a compound as a raw material for a polycarbonate resin or an epoxy resin allows for providing flexibility to the resulting resin. Further, it is also expected that a specific low water absorbency and chemical resistance can be imparted to the resulting resin, because the long chain alkyl group serves to increase lipophilicity. Therefore, the polyhydric phenol compounds as described above can be suitably used as raw materials for polycarbonate resins, which are used in automobile materials, electric and electronic device materials, house and building materials, materials for producing parts in other industrial fields, and the like, or as raw materials for epoxy resins, which are used in adhesive agents, coatings, civil engineering and construction materials, insulating materials for parts of electric and electronic devices, sealing materials, and the like.

In the field of parts of electric and electronic devices, in particular, there is a growing demand for devices having a smaller size and a higher performance, in recent years. With such a demand, resin materials to be used for these devices are required to have an improved flexibility, heat resistance and water absorbency. Therefore, the above described polyhydric phenol compounds capable of producing resins which satisfy such performances are extremely useful.

Further, the polyhydric phenol compounds containing a long chain alkyl group can also be widely used as additives for use in photosensitive materials, such as color developers and photoresists, taking advantage of their properties, such as a specific solubility in other solvents or additives due to containing the long chain alkyl group, and a low melting point.

PRIOR ART REFERENCES

Patent Document

Patent Document 1: JP 59-131623 A

Non-Patent Document

Non-patent Document: 1 Journal of the Chemical Society of Japan, Vol 59, Issue 8 (1956)

SUMMARY OF THE INVENTION

Problems to be Solved by the Invention

However, when the present inventors have investigated the performance of a polyhydric phenol compound such as one proposed in the above described Non-patent Document 1 or Patent Document 1 as a resin raw material or a color developer, it has been found out that the polyhydric phenol compound obtained by the method described in Non-patent Document 1 or Patent Document 1 has a problem of having a low alkali stability. The use of a conventional polyhydric phenol compound having a poor alkali stability as a resin raw material has a fatal drawback that it fails to provide a resin having a good color.

For example, in the case of using such a polyhydric phenol compound as a raw material for an epoxy resin, a precursor monomer is obtained by carrying out an addition reaction of the polyhydric phenol compound with epichlorohydrin under strong basic conditions, using sodium hydroxide or the like. At this time, if the polyhydric phenol compound has a low alkali stability, it may cause coloration of the precursor monomer, which in turn results in the coloration of the epoxy resin obtained using the monomer.

As methods for producing a polycarbonate resin, interfacial polymerization and melt transesterification are known, as disclosed in JP 2015-227416 A, for example. In the interfacial polymerization, a polyhydric phenol compound is formed into an aqueous alkaline solution (in particular, using a strongly basic hydroxide such as sodium hydroxide), and the resultant is then allowed to react with phosgene. In the melt transesterification, a polycondensation reaction of a polyhydric phenol compound and diphenyl carbonate is carried out in the presence of a basic catalyst, in a molten state. However, both of these methods fail to prevent the occurrence of a marked coloration in the resulting resin, if the polyhydric phenol compound has a low alkali stability.

Further, when such a polyhydric phenol compound is used as a color developer, in combination with an alkaline dye and/or an additive, changes in the color also occurs in the resulting resin, making the compound unsuitable for a practical use.

In view of the above described problems, an object of the present invention is to provide a polyhydric phenol compound which has an excellent alkali resistance and which does not cause a deterioration in color even when used as a resin raw material or a color developer.

Means for Solving the Problems

As a result of intensive studies, the present inventors have found out that it is possible to improve the alkali resistance of a polyhydric phenol compound, by allowing the polyhydric phenol compound to contain a bisphenol compound and a specific trisphenol compound such that the trisphenol compound is contained at a specific ratio with respect to the amount of the bisphenol compound, thereby completing the present invention.

Specifically, the gist the present invention resides, in the following [1] to [14].

[1] A polyhydric phenol compound including: a bisphenol compound (A) represented by the following Formula (1):

[Chem. 1]

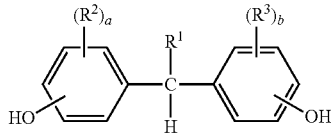

(1)

[wherein in Formula (1), $R^1$ represents a monovalent aliphatic hydrocarbon group having from 6 to 24 carbon atoms; each of $R^2$ and $R^3$ independently represents a monovalent hydrocarbon group having from 1 to 15 carbon atoms; each of a and b independently represents an integer from 0 to 4; and in cases where a and/or b are/is 2 or more, two or more $R^2$s and/or $R^3$s (respectively) present on the same benzene ring(s) are optionally bound to each other to form a ring(s) condensed to the benzene ring(s)];
and
a trisphenol compound (B) represented by the following Formula (2):

[Chem. 2]

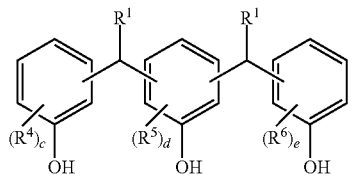

(2)

[wherein in Formula (2), $R^1$ is the same as defined in the Formula (1); each of $R^4$, $R^5$ and $R^6$ independently represents a monovalent hydrocarbon group having from 1 to 15 carbon atoms; each of c, d and e independently represents an integer from 0 to 4; and in cases where c, d and/or e are/is 2 or more, two or more $R^4$s, $R^5$s and/or $R^6$s (respectively) present on the same benzene ring(s) are optionally bound to each other to form a hydrocarbon ring(s) condensed to the benzene ring(s)];

wherein the trisphenol compound (B) is contained in an amount, in terms of absorption intensity ratio at 254 nm, of less than 1.6% by area with respect to the amount of the bisphenol compound (A).

[2] The polyhydric phenol compound according to [1], wherein the trisphenol compound (B) is contained in an amount, in terms of absorption intensity ratio at 254 nm, of 0.003% by area or more.

[3] The polyhydric phenol compound according to [2], wherein the trisphenol compound (B) is contained in an amount, in terms of absorption intensity ratio at 254 nm, of 0.06% by area or more and less than 1.6% by area.

[4] The polyhydric phenol compound according to any one of [1] to [3], wherein the bisphenol compound (A) is a mixture of a bisphenol compound (a1) represented by the following Formula (3) and a bisphenol compound (a2) represented by the following Formula (4):

[Chem. 3]

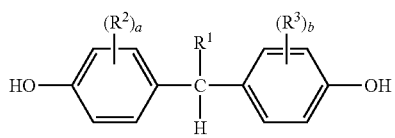

(3)

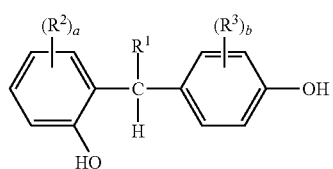

(4)

[wherein in Formulae (3) and (4), $R^1$, $R^2$, $R^3$, a and b are the same as defined in the Formula (1)], and wherein the ratio of the amount of the bisphenol compound (a2) with respect to the total amount of the bisphenol compound (a1) and the bisphenol compound (a2), in terms of absorption intensity ratio at 254 nm, is less than 1.5% by area.

[5] The polyhydric phenol compound according to any one of [1] to [4], wherein $R^1$ has from 10 to 18 carbon atoms.

[6] The polyhydric phenol compound according to any one of [1] to [5], wherein each of a, b, c, d and e is 0.

[7] A method of producing a polyhydric phenol compound, including producing the polyhydric phenol compound according to any one of [1] to [6] by allowing an aldehyde compound represented by the following Formula (15):

[Chem. 4]

(15)

[wherein in Formula (15), R$^1$ is the same as defined in the Formula (1)]
to react with a monophenol compound represented by the following Formula (16):

[Chem. 5]

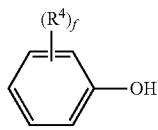
(16)

[wherein in Formula (16), R$^4$ is the same as defined in the Formula (2); and f represents an integer from 0 to 4].
[8] The method of producing a polyhydric phenol compound according to [7], including the step of purifying the polyhydric phenol compound and at least one hydrocarbon solvent.
[9] A resin obtained by polymerizing the polyhydric phenol compound according to any one of [1] to [6].
[10] The resin according to [9], wherein the resin is a polycarbonate resin.
[11] A method of producing a resin, including polymerizing the polyhydric phenol compound according to any one of [1] to [6], in the presence of an alkaline catalyst.
[12] The method of producing a resin according to [11], which is a method of producing a polycarbonate resin.
[13] The method of producing a resin according to [12], including producing the polycarbonate resin by interfacial polymerization or melt transesterification.
[14] Use of the polyhydric phenol compound according to any one of [1] to [6], as a color developer.

Effect of the Invention

Since the polyhydric phenol compound according to the present invention has an excellent alkali resistance, the use of the polyhydric phenol compound as a resin raw material enables to provide functionalities such as flexibility, etc., to the resulting resin, with a high productivity and without causing a deterioration in color. For example, by using the polyhydric phenol compound according to the present invention as a raw material for a thermoplastic resin such as a polycarbonate resin, or a thermosetting resin such as an epoxy resin, it is possible to improve the flexibility, the low water absorbency and the chemical resistance of the resulting resin, without markedly impairing the good mechanical properties and thermal properties inherent in the resin, and while preventing a deterioration in color due to coloration. Further, when the polyhydric phenol compound according to the present invention is used as a color developer in a thermosensitive recording material or the like, it is possible to obtain a material having an intended color, with a good reproducibility.

In addition, when used as a resin raw material, the polyhydric phenol compound can be formed into a monomer material having a high flowability, and it allows for omitting steps such as grinding and classification steps, due to having excellent powder properties.

Mode for Carrying Out the Invention

The embodiments of the present invention will now be described in detail. It is to be noted, however, that each of the constitutions described below is an example of the embodiments of the present invention, and that the present invention is not limited to the following description unless the gist of the invention is deviated. Further, in cases where the expression "from * to" is used to refer to a range in the present specification, numerical values or physical property values described before and after the "to" are included in the range described by the expression.
[Polyhydric Phenol Compound]
The polyhydric phenol compound according to the present invention is characterized by including:
a bisphenol compound (A) represented by the following Formula (1):

[Chem. 6]

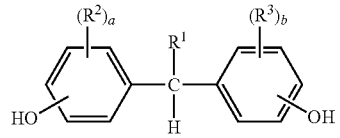
(1)

[wherein in Formula (1), R$^1$ represents a monovalent aliphatic hydrocarbon group having from 6 to 24 carbon atoms; each of R$^2$ and R$^3$ independently represents a ion valent hydrocarbon group having from 1 to 15 carbon atoms; each of a and b independently represents an integer from 0 to 4; and in cases where a and/or b are/is 2 or more, two or more R$^2$s and/or R$^3$s (respectively) present on the same benzene ring(s) are optionally bound to each other to form a ring(s) condensed to the benzene ring(s)];
and
a trisphenol compound (B) represented by the following Formula (2):

[Chem. 7]

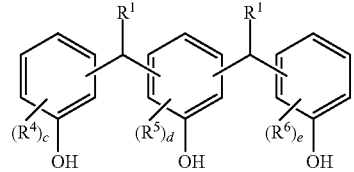
(2)

[wherein in Formula (2), R$^1$ is the same as defined in the Formula (1); each of R$^4$, R$^5$ and R$^6$ independently represents a monovalent hydrocarbon group having from 1 to 15 carbon atoms; each of c, d and e independently represents an integer from 0 to 4; and in cases where c, d and/or e are/is 2 or more, two or more R$^4$s, R$^5$s and/or R$^6$s (respectively) present on the same benzene ring(s) are optionally bound to each other to form a hydrocarbon ring(s) condensed to the benzene ring(s)];
wherein the trisphenol compound (B) is contained in an amount, in terms of absorption intensity ratio at 254 nm, of less than 1.6% by area with respect to the amount of the bisphenol compound (A).

In Formulae (1) and (2), $R^1$ represents a monovalent aliphatic hydrocarbon group having from 6 to 24 carbon atoms. Examples of the aliphatic hydrocarbon group as used herein include: alkyl groups, which are saturated aliphatic hydrocarbon groups; and alkenyl groups, alkynyl groups and alkadienyl groups, which are unsaturated aliphatic hydrocarbon groups.

In cases where $R^1$ is a monovalent aliphatic hydrocarbon group having 6 or more carbon atoms, the use of the polyhydric phenol compound as a resin raw material enables to provide a good flexibility, low water absorbency and chemical resistance to the resulting resin. Further, the polyhydric phenol compound exhibits a low melting point, and thus can be suitably used as a specific color developer, as well. In view of the above, the above described $R^1$ preferably has 9 or more carbon atoms, more preferably 10 or more carbon atoms, and still more preferably 11 or more carbon atoms.

In cases where $R^1$ has more than 24 carbon atoms, however, the use of the polyhydric phenol compound as a resin raw material tends to result in a marked decrease in the heat resistance and mechanical strength of the resulting resin, and thus is not preferred. Further, the polyhydric phenol compound has too high a melting point, leading to a decrease in function as a color developer, which is also not preferred. In view of the above, the above described $R^1$ preferably has 22 or less carbon atoms, more preferably 18 or less carbon atoms, and still more preferably 16 or less carbon atoms.

Preferred examples of the monovalent aliphatic hydrocarbon group having from 6 to 24 carbon atoms, which is represented by $R^1$, include a linear or branched alkyl group, an alkyl group having a partially cyclic structure, and an alkenyl group. Among these, the monovalent aliphatic hydrocarbon group is more preferably a linear or branched alkyl group, and still more preferably a linear alkyl group, since the flexibility of the resulting resin can be more effectively improved.

Specific examples of the linear alkyl group include n-hexyl group, n-heptyl group, n-octyl group, n-nonyl group, n-decyl group, n-undecyl group, n-dodecyl group, n-tridecyl group, n-tetradecyl group, n-pentadecyl group, n-hexadecyl group, n-heptadecyl group, n-octadecyl group, n-nonadecyl group, n-icosyl group, n-henicosyl group, n-docosyl group, n-tricosyl group and n-tetracosyl group. The linear alkyl group is preferably n-nonyl group, n-decyl group, n-undecyl group, n-dodecyl group, n-hexadecyl group or n-octadecyl group, more preferably n-undecyl group or n-dodecyl group, and particularly preferably n-dodecyl group.

Specific examples of the branched alkyl group include:

methylpentyl group, methylhexyl group, methylheptyl group, methyloctyl group, methylnonyl group, methyldecyl group, methylundecyl group, methyldodecyl group, methyltridecyl group, methyltetradecyl group, methylpentadecyl group, methylhexadecyl group, methylheptadecyl group, methyloctadecyl group, methylnonadecyl group, methylicosyl group, methylicosyl group, methylhenicosyl group, methyldocosyl group and methyltricosyl group;

dimethylbutyl group, dimethylpentyl group, dimethylhexyl group, dimethylheptyl group, dimethyloctyl group, dimethylnonyl group, dimethyldecyl group, dimethylundecyl group, dimethyldodecyl group, dimethyltridecyl group, dimethyltetradecyl group, dimethylpentadecyl group, dimethylhexadecyl group, dimethylheptadecyl group, dimethyloctadecyl group, dimethylnonadecyl group, dimethylicosyl group, dimethylicosyl group, dimethylhenicosyl group and dimethyldocosyl group;

trimethylhexyl group, trimethylheptyl group, trimethyloctyl group, trimethylnonyl group, trimethyldecyl group, trimethylundecyl group, trimethyldodecyl group, trimethyltridecyl group, trimethyltetradecyl group, trimethylpentadecyl group, trimethylhexadecyl group, trimethylheptadecyl group, trimethyloctadecyl group, trimethylnonadecyl group, trimethylicosyl group, trimethylicosyl group and trimethylhenicosyl group;

ethylpentyl group, ethylhexyl group, ethylheptyl group, ethyloctyl group, ethylnonyl group, ethyldecyl group, ethylundecyl group, ethyldodecyl group, ethyltridecyl group, ethyltetradecyl group, ethylpentadecyl group, ethylhexadecyl group, ethylheptadecyl group, ethyloctadecyl group, ethylnonadecyl group, ethylicosyl group, ethylicosyl group, ethylhenicosyl group and ethyldocosyl group;

propylhexyl group, propylheptyl group, propyloctyl group, propylnonyl group, propyldecyl group, propylundecyl group, propyldodecyl group, propyltridecyl group, propyltetradecyl group, propylpentadecyl group, propylhexadecyl group, propylheptadecyl group, propyloctadecyl group, propylnonadecyl group, propylicosyl group, propylicosyl group and propylhenicosyl group; and butylhexyl group, butylheptyl group, butyloctyl group, butylnonyl group, butyldecyl group, butylundecyl group, butyldodecyl group, butyltridecyl group, butyltetradecyl group, butylpentadecyl group, butylhexadecyl group, butylheptadecyl group, butyloctadecyl group, butylnonadecyl group, butylicosyl group and butylicosyl group.

Among these, the branched alkyl group is preferably a branched alkyl group having from 7 to 17 carbon atoms, such as ethylpentyl group, ethylhexyl group, ethylheptyl group, ethyloctyl group, ethylundecyl group or ethylpentadecyl group, more preferably ethylpentyl group or ethylhexyl group, and particularly preferably ethylpentyl group.

It is to be noted that, in the above described examples of the branched alkyl group, the position of the branching is arbitrary.

Specific examples of the alkyl group having a partially cyclic structure include:

cyclohexyl group, cycloheptyl group, cyclooctyl group, cyclononyl group, cyclodecyl group, cycloundecyl group and cyclododecyl group;

cyclohexylmethyl group, cycloheptylmethyl group, cyclooctylmethyl group, cyclononylmethyl group, cyclodecylmethyl group, cycloundecylmethyl group and cyclododecylmethyl group;

cyclohexylethyl group, cycloheptylethyl group, cyclooctylethyl group, cyclononylethyl group, cyclodecylethyl group, cycloundecylethyl group and cyclododecyl ethyl group;

cyclohexylpropyl group, cycloheptylpropyl group, cyclooctylpropyl group, cyclononylpropyl group, cyclohexylpropyl group, cycloundecylpropyl group and cyclododecylpropyl group;

methylcyclohexyl group, methylcycloheptyl group, methylcyclooctyl group, methylcyclononyl group, methylcyclodecyl group, methylcycloundecyl group and methylcyclododecyl group;

dimethylcyclohexyl group, dimethylcycloheptyl group, dimethylcyclooctyl group, dimethylcyclononyl group, dimethylcyclodecyl group, dimethylcycloundecyl group and dimethylcyclododecyl group;

ethylcyclohexyl group, ethylcycloheptyl group, ethylcyclooctyl group, ethylcyclononyl group, ethylcyclodecyl group, ethylcycloundecyl group and ethylcyclododecyl group;

propylcyclohexyl group, propylcycloheptyl group, propylcyclooctyl group, propylcyclononyl group, propylcyclodecyl group, propylcycloundecyl group and propylcyclododecyl group;

hexylcyclohexyl group, hexylcycloheptyl group, hexylcyclooctyl group, hexylcyclononyl group, hexylcyclodecyl group, hexylcycloundecyl group and hexylcyclododecyl group;

(methylcyclohexyl)methyl group, (methylcycloheptyl)methyl group, (methylcyclooctyl)methyl group, (methylcyclononyl)methyl group, (methylcyclodecyl)methyl group, (methylcycloundecyl)methyl group and (methylcyclododecyl)methyl group;

(methylcyclohexyl)ethyl group, (methylcycloheptyl)ethyl group, (methylcyclooctyl)ethyl group, (methylcyclononyl)ethyl group, (methylcyclodecyl)ethyl group, (methylcycloundecyl)ethyl group and (methylcyclododecyl)ethyl group;

(methylcyclohexyl)propyl group, (methylcycloheptyl)propyl group, (methylcyclooctyl)propyl group, (methylcyclononyl)propyl group, (methylcyclodecyl)propyl group, (methylcycloundecyl)propyl group and (methylcyclododecyl)propyl group;

(dimethylcyclohexyl)methyl group, (dimethylcycloheptyl)methyl group, (dimethylcyclooctyl)methyl group, (dimethylcyclononyl)methyl group, (dimethylcyclodecyl)methyl group, (dimethylcycloundecyl)methyl group and (dimethylcyclododecyl)methyl group;

(dimethylcyclohexyl)ethyl group, (dimethylcycloheptyl)ethyl group, (dimethylcyclooctyl)ethyl group, (dimethylcyclononyl)ethyl group, (dimethylcyclodecyl)ethyl group, (dimethylcycloundecyl)ethyl group and (dimethylcyclododecyl)ethyl group; and (dimethylcyclohexyl)propyl group, (dimethylcycloheptyl)propyl group, (dimethylcyclooctyl)propyl group, (dimethylcyclononyl)propyl group, (dimethylcyclodecyl)propyl group, (dimethylcycloundecyl)propyl group, (dimethylcyclododecyl)propyl group and cyclohexylcyclohexyl group.

Among these, the alkyl group having a partially cyclic structure is preferably a cyclic alkyl group having from 6 to 10 carbon atoms, such as cyclohexyl group, cycloheptyl group, cyclooctyl group, cyclononyl group, cyclodecyl group, cyclohexylmethyl group, cycloheptylmethyl group, cyclooctylmethyl group, cyclononylmethyl group, cyclohexylethyl group, cycloheptylethyl group, cyclooctylethyl group, cyclohexylmethyl group, cycloheptylmethyl group or cyclooctylmethyl group, or alternatively, an alkyl group having a cyclic alkyl group as a substituent, more preferably cyclohexyl group, cycloheptyl group or cyclooctyl group, and particularly preferably cyclohexyl group.

It is to be noted that, in the above described examples of the alkyl group having a partially cyclic structure, the position of the substituent is arbitrary.

The unsaturated aliphatic hydrocarbon group represented by $R^1$, such as an alkenyl group or an alkadienyl group, is not particularly limited, as long as it is any of the linear alkyl group, the branched alkyl group, and the alkyl group having a partially cyclic structure, as described above, which contains one or more carbon-carbon double bonds in its structure. Specific examples thereof include hexenyl group, heptynyl group, octenyl group, nonenyl group, decenyl group, undecenyl group, dodecenyl group, tridecenyl group, tetradecenyl group, pentadecenyl group, hexadecenyl group, heptadecenyl group, octadecenyl group, nonadecenyl group, icosenyl group, henicosenyl group, docosenyl group, tricosenyl group, tetracosenyl group, 4,8,12-trimethyltridecyl group and bicyclo[2,2,1]hept-5-en-2-yl group.

Each of $R^2$ and $R^3$ in Formula (1), and each of $R^4$, $R^5$ and $R^6$ in Formula (2), independently represents a monovalent hydrocarbon group having from 1 to 15 carbon atoms.

When a monovalent hydrocarbon group having from 1 to 15 carbon atoms is contained, the use of the polyhydric phenol compound according to the present invention as a resin raw material enables to improve the flowability, strength, hardness, chemical resistance and the like of the resulting resin. Further, it becomes possible to alter the solubility of the polyhydric phenol compound in a specific solvent or additive, and also to control the physical properties of the compound depending on the intended purpose, when used as a raw material for various types of materials, such as a color developer, or as an additive.

The monovalent hydrocarbon group having from 1 to 15 carbon atoms may be a saturated hydrocarbon group or an unsaturated hydrocarbon group, and may be an aliphatic hydrocarbon group or an aromatic hydrocarbon group. Examples thereof include an alkyl group having from 1 to 15 carbon atoms and an alkenyl group having from 2 to 15 carbon atoms. Such a hydrocarbon group may be a linear or branched group, or may be a cyclic group. Specific examples of the monovalent hydrocarbon group as described above include methyl group, ethyl group, propyl group, isopropyl group, n-butyl group, isobutyl group, sec-butyl group, tert-butyl group, pentyl group, n-hexyl group, cyclohexyl group, n-heptyl group, n-octyl group, n-nonyl group, n-decyl group, n-undecyl group, n-dodecyl group, n-tridecyl group, n-tetradecyl group, n-pentadecyl group, phenyl group and tolyl group. Among these, methyl group is preferred. In cases where two or more $R^2$s, $R^3$s, $R^4$s, $R^5$s and/or $R^6$s are (respectively) present on the same benzene ring(s), the (respective) two or more $R^2$s, $R^3$s, $R^4$s, $R^5$s and/or $R^6$s may be the same as, or different from, each other. Alternatively, two of (each of) the two or more $R^2$s, $R^3$s, $R^4$s, $R^5$s and/or $R^6$s are optionally bound to each other to form a ring condensed to the benzene ring.

Each of a and b in Formula (1), and each of c, d and e in Formula (2), independently represents an integer from 0 to 4, and is preferably 0 to 2, more preferably 0 to 1, and still more preferably 0, in particular. When a, b, c, d and e are within the above described range, the use of the polyhydric phenol compound according to the present invention enables to produce a resin having a good color.

In the polyhydric phenol compound according to the present invention, it is important, as described above, that the trisphenol compound (B) is contained in an amount, in terms of absorption intensity ratio at 254 nm, of less than 1.6% by area with respect to the amount of the bisphenol compound (A). By incorporating the trisphenol compound (B) in such a ratio, it is thought that the low water absorbency and the chemical resistance of the resulting resin can further be improved, when the polyhydric phenol compound according to the present invention is used as a raw material. Further, when the polyhydric phenol compound is used as a color developer, the compound is thought to exhibit a good solubility in various types of additives and solvents. A content of the trisphenol compound (B) of 1.6% by area or more is not preferred, because the alkali stability of the polyhydric phenol compound is extremely decreased, to cause coloration. When the polyhydric phenol compound is used as a raw material for a resin, such a content may lead to risks of an increased melt viscosity and increased amounts of gel and foreign substances, and is also not preferred. In view of the above, the content of the trisphenol compound (B) in the polyhydric phenol compound according to the present invention is preferably 1.5% by area or less, more preferably 1.2% by area or less, still more preferably 1.0% by area or less, particularly preferably 0.7% by area or less, and most preferably 0.5% by area or less in terms of absorption intensity ratio at 254 nm, with respect to the amount of the bisphenol compound (A). The lower limit of the content of the trisphenol compound (B) is preferably, but not limited to, 0.001% by area or more, more preferably 0.003% by area or more, still more preferably 0.005% by area or more, further still more preferably 0.01% by area or more, particularly preferably 0.02% by area or more, especially preferably 0.05% by area or more, further especially preferably 0.06% by area or more, and most preferably 0.10% by area or more.

Incorporation of the trisphenol compound (B) in such a ratio is preferred, because it enables to obtain the polyhydric phenol compound according to the present invention as a powder having an adequate particle size, without carrying out special treatments such as grinding and classification in the production of the polyhydric phenol compound according to the present invention, and tends to result in a decrease in load and the like in a solvent removal step to be described later. In particular, by adjusting the content of the trisphenol compound (B) to 0.06% by area or more, it is possible to prevent an extreme increase in the load in the solvent removal step resulting from an extreme increase in the particle size, in the production of the polyhydric phenol compound according to the present invention. In view of the above, the content of the trisphenol compound (B) in the polyhydric phenol compound according to the present invention is preferably 0.07% by area or more, more preferably 0.08% by area or more, particularly preferably 0.09% by area or more, and most preferably 0.10% by area or more in terms of absorption intensity ratio at 254 nm, with respect to the amount of the bisphenol compound (A).

The absorption intensity ratio at 254 nm can be obtained as follows: a quantity of 20 mg of the polyhydric phenol compound according to the present invention is dissolved in 100 ml of acetonitrile; 5 μl of the resulting solution is then eluted using as an eluent a mixed liquid of acetonitrile and a 0.1% by mass aqueous solution of ammonium acetate; the measurement and analysis are carried out under the following conditions, to determine the areas of the peaks corresponding to the respective compounds; and the area ratio of the respective peaks is calculated to be used as the absorption intensity ratio at 254 nm.

(Measurement Conditions)

Controller: SCL-10AVP, manufactured by Shimadzu Corporation

Column: inertsil ODS3V (4.6×150 mm, 5 μm), manufactured by GL Sciences Inc.

Column oven: CTO-10AVP, manufactured by Shimadzu Corporation; 40° C.

Pump: LC-10ADVP, manufactured by Shimadzu Corporation; flow rate: 1.0 ml/min

Elution conditions: K1=acetonitrile, K2=a 0.1% by mass aqueous solution of ammonium acetate K1/K2=60/40 (0 to 5 minutes)

K1/K2=60/40→95/5 (linear concentration change, 5 to 30 minutes)

K1/K2=95/5 (30 to 80 minutes)

(ratio: volume ratio)

Detector: SPD-10AVP, manufactured by Shimadzu Corporation; UV 254 nm (Analysis Conditions)

Software: LC-solution ver. 1.22 SP1, manufactured by Shimadzu Corporation

Settings: Width=5, Slope=200, Drift=0, T. DBL=1,000, Min. Area=500

Under the above described conditions, the peaks corresponding to the bisphenol compound (A) and the trisphenol compound (B) can be easily identified by: isolating the components corresponding to the respective peaks by an ordinary means such as silica gel column chromatography; and then carrying out an analysis by an ordinary analysis means such as nuclear magnetic resonance analysis (NMR) or liquid phase chromatography-mass spectrometry (LC-MS). Further, the trisphenol compound (B) is usually a mixture of a plurality of types of compounds differing in the position of substitution; therefore, in the present invention, the respective peak areas are added to obtain the absorption peak area of the trisphenol compound (B).

The bisphenol compound (A) (hereinafter, sometimes referred to as the "bisphenol compound (A) according to the present invention") contained in the polyhydric phenol compound in the present invention may be, specifically, a mixture of a bisphenol compound (a1) represented by the following Formula (3), a bisphenol compound (a2) represented by the following Formula (4), and a bisphenol compound (a3) represented by a the following Formula (5).

[Chem. 8]

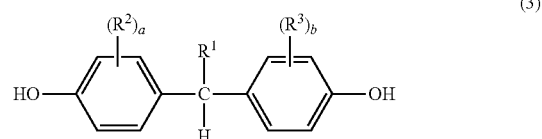

(3)

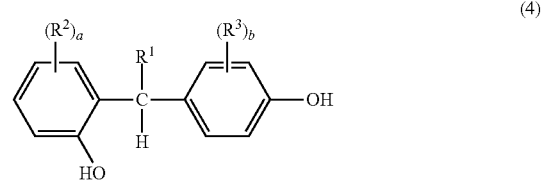

(4)

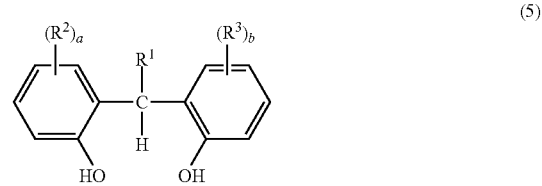

(5)

In Formulae (3), (4) and (5), $R^1$, $R^2$, $R^3$, a and b are the same defined in the Formula (1).

Examples of $R^1$, $R^2$, $R^3$, a and b in the bisphenol compound (a1) represented by the Formula (3) include the compounds shown in the following Tables 1a to 1d. Further, examples of $R^1$, $R^2$, $R^3$, a and b in the bisphenol compound (a2) represented by the Formula (4) include the compounds shown in the following Tables 2a to 2d. Examples of $R^1$, $R^2$, $R^3$, a and b in the bisphenol compound (a3) represented by the Formula (5) include the compounds shown in the following Tables 3a to 3d.

TABLE 1d

| Compound | R¹ | R² | R³ | a | b |
|---|---|---|---|---|---|
| p-1-1 | n-hexyl | — | — | 0 | 0 |
| p-1-2 | n-heptyl | — | — | 0 | 0 |
| p-1-3 | n-octyl | — | — | 0 | 0 |
| p-1-4 | n-nonyl | — | — | 0 | 0 |
| p-1-5 | n-decyl | — | — | 0 | 0 |
| p-1-6 | n-undecyl | — | — | 0 | 0 |
| p-1-7 | n-dodecyl | — | — | 0 | 0 |
| p-1-8 | n-tridecyl | — | — | 0 | 0 |
| p-1-9 | n-tetradecyl | — | — | 0 | 0 |
| p-1-10 | n-pentadecyl | — | — | 0 | 0 |
| p-1-11 | n-hexadecyl | — | — | 0 | 0 |
| p-1-12 | n-heptadecyl | — | — | 0 | 0 |
| p-1-13 | n-octadecyl | — | — | 0 | 0 |
| p-1-14 | n-nonadecyl | — | — | 0 | 0 |
| p-1-15 | n-icosyl | — | — | 0 | 0 |
| p-1-16 | n-eicosyl | — | — | 0 | 0 |
| p-1-17 | n-henicosyl | — | — | 0 | 0 |
| p-1-18 | n-docosyl | — | — | 0 | 0 |
| p-1-19 | n-tricosyl | — | — | 0 | 0 |
| p-1-20 | n-tetracosyl | — | — | 0 | 0 |
| p-1-21 | 1-ethylpentyl | — | — | 0 | 0 |
| p-1-22 | 2,4,4-trimethylpentyl | — | — | 0 | 0 |
| p-1-23 | 3-hexenyl | — | — | 0 | 0 |
| p-1-24 | 9-decenyl | — | — | 0 | 0 |
| p-1-25 | 10-pentadecyl | — | — | 0 | 0 |
| p-1-25 | 1-ethyl-1-pentenyl | — | — | 0 | 0 |
| p-1-27 | 1,5-dimethyl-4-hexenyl | — | — | 0 | 0 |
| p-1-28 | 2,6-dimethyl-5-heptenyl | — | — | 0 | 0 |
| p-1-29 | cyclohexyl | — | — | 0 | 0 |

TABLE 1b

| Compound | R¹ | R² | R³ | a | b |
|---|---|---|---|---|---|
| p-1-30 | 3-cyclohexenyl | — | — | 0 | 0 |
| p-1-31 | n-hexyl | methyl | methyl | 1 | 1 |
| p-1-32 | n-octyl | methyl | methyl | 1 | 1 |
| p-1-33 | n-nonyl | methyl | methyl | 1 | 1 |
| p-1-34 | n-decyl | methyl | methyl | 1 | 1 |
| p-1-35 | n-undecyl | methyl | methyl | 1 | 1 |
| p-1-36 | n-dodecyl | methyl | methyl | 1 | 1 |
| p-1-37 | 1-ethylpentyl | methyl | methyl | 1 | 1 |
| p-1-38 | n-octyl | ethyl | ethyl | 1 | 1 |
| p-1-39 | n-nonyl | ethyl | ethyl | 1 | 1 |
| p-1-40 | n-decyl | ethyl | ethyl | 1 | 1 |
| p-1-41 | n-undecyl | ethyl | ethyl | 1 | 1 |
| p-1-42 | 1-ethylpentyl | ethyl | ethyl | 1 | 1 |
| p-1-43 | n-octyl | iso-propyl | iso-propyl | 1 | 1 |
| p-1-44 | n-nonyl | iso-propyl | iso-propyl | 1 | 1 |
| p-1-45 | n-decyl | iso-propyl | iso-propyl | 1 | 1 |
| p-1-46 | n-undecyl | iso-propyl | iso-propyl | 1 | 1 |
| p-1-47 | 1-ethylpentyl | iso-propyl | iso-propyl | 1 | 1 |
| p-1-48 | n-octyl | allyl | allyl | 1 | 1 |
| p-1-49 | n-nonyl | allyl | allyl | 1 | 1 |
| p-1-50 | n-decyl | allyl | allyl | 1 | 1 |
| p-1-51 | n-undecyl | allyl | allyl | 1 | 1 |
| p-1-52 | 1-ethylpentyl | allyl | allyl | 1 | 1 |
| p-1-53 | n-octyl | sec-butyl | sec-butyl | 1 | 1 |
| p-1-54 | n-nonyl | sec-butyl | sec-butyl | 1 | 1 |
| p-1-55 | n-decyl | sec-butyl | sec-butyl | 1 | 1 |
| p-1-56 | n-undecyl | sec-butyl | sec-butyl | 1 | 1 |
| p-1-57 | 1-ethylpentyl | sec-butyl | sec-butyl | 1 | 1 |

TABLE 1c

| Compound | R¹ | R² | R³ | a | b |
|---|---|---|---|---|---|
| p-1-58 | n-octyl | tert-butyl | tert-butyl | 1 | 1 |
| p-1-59 | n-nonyl | tert-butyl | tert-butyl | 1 | 1 |
| p-1-60 | n-decyl | tert-butyl | tert-butyl | 1 | 1 |
| p-1-61 | n-undecyl | tert-butyl | tert-butyl | 1 | 1 |
| p-1-62 | 1-ethylpentyl | tert-butyl | tert-butyl | 1 | 1 |
| p-1-63 | n-octyl | tert-amyl | tert-amyl | 1 | 1 |
| p-1-64 | n-nonyl | tert-amyl | tert-amyl | 1 | 1 |
| p-1-65 | n-decyl | tert-amyl | tert-amyl | 1 | 1 |
| p-1-66 | n-undecyl | tert-amyl | tert-amyl | 1 | 1 |
| p-1-67 | 1-ethylpentyl | tert-amyl | tert-amyl | 1 | 1 |
| p-1-68 | n-octyl | n-nonyl | n-nonyl | 1 | 1 |
| p-1-69 | n-nonyl | n-nonyl | n-nonyl | 1 | 1 |
| p-1-70 | n-decyl | n-nonyl | n-nonyl | 1 | 1 |
| p-1-71 | n-undecyl | n-nonyl | n-nonyl | 1 | 1 |
| p-1-72 | 1-ethylpentyl | n-nonyl | n-nonyl | 1 | 1 |
| p-1-73 | n-octyl | n-dodecyl | n-dodecyl | 1 | 1 |
| p-1-74 | n-nonyl | n-dodecyl | n-dodecyl | 1 | 1 |
| p-1-75 | n-decyl | n-dodecyl | n-dodecyl | 1 | 1 |
| p-1-76 | n-undecyl | n-dodecyl | n-dodecyl | 1 | 1 |
| p-1-77 | 1-ethylpentyl | n-dodecyl | n-dodecyl | 1 | 1 |
| p-1-78 | n-octyl | cyclohexyl | cyclohexyl | 1 | 1 |
| p-1-79 | n-nonyl | cyclohexyl | cyclohexyl | 1 | 1 |
| p-1-80 | n-decyl | cyclohexyl | cyclohexyl | 1 | 1 |
| p-1-81 | n-octyl | phenyl | phenyl | 1 | 1 |
| p-1-82 | n-nonyl | phenyl | phenyl | 1 | 1 |
| p-1-83 | n-decyl | phenyl | phenyl | 1 | 1 |
| p-1-84 | n-octyl | benzyl | benzyl | 1 | 1 |
| p-1-85 | n-nonyl | benzyl | benzyl | 1 | 1 |

TABLE 1d

| Compound | R¹ | R² | R³ | a | b |
|---|---|---|---|---|---|
| p-1-86 | n-decyl | benzyl | benzyl | 1 | 1 |
| p-1-87 | n-octyl | methyl | methyl | 2 | 2 |
| p-1-88 | n-nonyl | methyl | methyl | 2 | 2 |
| p-1-89 | n-decyl | methyl | methyl | 2 | 2 |
| p-1-90 | n-octyl | ethyl | ethyl | 2 | 2 |
| p-1-91 | n-nonyl | ethyl | ethyl | 2 | 2 |
| p-1-92 | n-decyl | ethyl | ethyl | 2 | 2 |
| p-1-93 | n-octyl | iso-propyl | iso-propyl | 2 | 2 |
| p-1-94 | n-nonyl | iso-propyl | iso-propyl | 2 | 2 |
| p-1-95 | n-decyl | iso-propyl | iso-propyl | 2 | 2 |
| p-1-96 | n-octyl | sec-butyl | sec-butyl | 2 | 2 |
| p-1-97 | n-nonyl | sec-butyl | sec-butyl | 2 | 2 |
| p-1-98 | n-decyl | sec-butyl | sec-butyl | 2 | 2 |
| p-1-99 | n-octyl | tert-butyl | tert-butyl | 2 | 2 |
| p-1-100 | n-nonyl | tert-butyl | tert-butyl | 2 | 2 |
| p-1-101 | n-decyl | tert-butyl | tert-butyl | 2 | 2 |
| p-1-102 | n-octyl | methyl | methyl | 3 | 3 |
| p-1-103 | n-nonyl | methyl | methyl | 3 | 3 |
| p-1-104 | n-decyl | methyl | methyl | 3 | 3 |
| p-1-105 | n-octyl | methyl | methyl | 1 | 0 |
| p-1-106 | n-nonyl | methyl | methyl | 1 | 0 |
| p-1-107 | n-decyl | methyl | methyl | 1 | 0 |
| p-1-108 | n-octyl | methyl | methyl | 2 | 0 |
| p-1-109 | n-nonyl | methyl | methyl | 2 | 0 |
| p-1-110 | n-decyl | methyl | methyl | 2 | 0 |
| p-1-111 | n-octyl | methyl | methyl | 2 | 1 |
| p-1-112 | n-nonyl | methyl | methyl | 2 | 1 |
| p-1-113 | n-decyl | methyl | methyl | 2 | 1 |

TABLE 2a

| Compound | R¹ | R² | R³ | a | b |
|---|---|---|---|---|---|
| p-2-1 | n-hexyl | — | — | 0 | 0 |
| p-2-2 | n-heptyl | — | — | 0 | 0 |
| p-2-3 | n-octyl | — | — | 0 | 0 |
| p-2-4 | n-nonyl | — | — | 0 | 0 |
| p-2-5 | n-decyl | — | — | 0 | 0 |
| p-2-6 | n-undecyl | — | — | 0 | 0 |
| p-2-7 | n-dodecyl | — | — | 0 | 0 |
| p-2-8 | n-tridecyl | — | — | 0 | 0 |
| p-2-9 | n-tetradecyl | — | — | 0 | 0 |
| p-2-10 | n-pentadecyl | — | — | 0 | 0 |
| p-2-11 | n-hexadecyl | — | — | 0 | 0 |
| p-2-12 | n-heptadecyl | — | — | 0 | 0 |
| p-2-13 | n-octadecyl | — | — | 0 | 0 |

TABLE 2a-continued

| Compound | R¹ | R² | R³ | a | b |
|---|---|---|---|---|---|
| p-2-14 | n-nonadecyl | — | — | 0 | 0 |
| p-2-15 | n-icosyl | — | — | 0 | 0 |
| p-2-16 | n-eicosyl | — | — | 0 | 0 |
| p-2-17 | n-henicosyl | — | — | 0 | 0 |
| p-2-18 | n-docosyl | — | — | 0 | 0 |
| p-2-19 | n-tricosyl | — | — | 0 | 0 |
| p-2-20 | n-tetracosyl | — | — | 0 | 0 |
| p-2-21 | 1-ethylpentyl | — | — | 0 | 0 |
| p-2-22 | 2,4,4-trimethylpentyl | — | — | 0 | 0 |
| p-2-23 | 3-hexenyl | — | — | 0 | 0 |
| p-2-24 | 9-decenyl | — | — | 0 | 0 |
| p-2-25 | 10-pentadecyl | — | — | 0 | 0 |
| p-2-26 | 1-ethyl-2-pentenyl | — | — | 0 | 0 |
| p-2-27 | 1,5-dimethyl-4-hexenyl | — | — | 0 | 0 |
| p-2-28 | 2,6-dimethyl-5-heptenyl | — | — | 0 | 0 |
| p-2-29 | cyclohexyl | — | — | 0 | 0 |

TABLE 2b

| Compound | R¹ | R² | R³ | a | b |
|---|---|---|---|---|---|
| p-2-30 | 3-cyclohexenyl | — | — | 0 | 0 |
| p-2-31 | n-hexyl | methyl | methyl | 1 | 1 |
| p-2-32 | n-octyl | methyl | methyl | 1 | 1 |
| p-2-33 | n-nonyl | methyl | methyl | 1 | 1 |
| p-2-34 | n-decyl | methyl | methyl | 1 | 1 |
| p-2-35 | n-undecyl | methyl | methyl | 1 | 1 |
| p-2-36 | n-dodecyl | methyl | methyl | 1 | 1 |
| p-2-37 | 1-ethylpentyl | methyl | methyl | 1 | 1 |
| p-2-38 | n-octyl | ethyl | ethyl | 1 | 1 |
| p-2-39 | n-nonyl | ethyl | ethyl | 1 | 1 |
| p-2-40 | n-decyl | ethyl | ethyl | 1 | 1 |
| p-2-41 | n-undecyl | ethyl | ethyl | 1 | 1 |
| p-2-42 | 1-ethylpentyl | ethyl | ethyl | 1 | 1 |
| p-2-43 | n-octyl | iso-propyl | iso-propyl | 1 | 1 |
| p-2-44 | n-nonyl | iso-propyl | iso-propyl | 1 | 1 |
| p-2-45 | n-decyl | iso-propyl | iso-propyl | 1 | 1 |
| p-2-46 | n-undecyl | iso-propyl | iso-propyl | 1 | 1 |
| p-2-47 | 1-ethylpentyl | iso-propyl | iso-propyl | 1 | 1 |
| p-2-48 | n-octyl | allyl | allyl | 1 | 1 |
| p-2-49 | n-nonyl | allyl | allyl | 1 | 1 |
| p-2-50 | n-decyl | allyl | allyl | 1 | 1 |
| p-2-51 | n-undecyl | allyl | allyl | 1 | 1 |
| p-2-52 | 1-ethylpentyl | allyl | allyl | 1 | 1 |
| p-2-53 | n-octyl | sec-butyl | sec-butyl | 1 | 1 |
| p-2-54 | n-nonyl | sec-butyl | sec-butyl | 1 | 1 |
| p-2-55 | n-decyl | sec-butyl | sec-butyl | 1 | 1 |
| p-2-56 | n-undecyl | sec-butyl | sec-butyl | 1 | 1 |
| p-2-57 | 1-ethylpentyl | sec-butyl | sec-butyl | 1 | 1 |

TABLE 2c

| Compound | R¹ | R² | R³ | a | b |
|---|---|---|---|---|---|
| p-2-58 | n-octyl | tert-butyl | tert-butyl | 1 | 1 |
| p-2-59 | n-nonyl | tert-butyl | tert-butyl | 1 | 1 |
| p-2-60 | n-decyl | tert-butyl | tert-butyl | 1 | 1 |
| p-2-61 | n-undecyl | tert-butyl | tert-butyl | 1 | 1 |
| p-2-62 | 1-ethylpentyl | tert-butyl | tert-butyl | 1 | 1 |
| p-2-63 | n-octyl | tert-amyl | tert-amyl | 1 | 1 |
| p-2-64 | n-nonyl | tert-amyl | tert-amyl | 1 | 1 |
| p-2-65 | n-decyl | tert-amyl | tert-amyl | 1 | 1 |
| p-2-66 | n-undecyl | tert-amyl | tert-amyl | 1 | 1 |
| p-2-67 | 1-ethylpentyl | tert-amyl | tert-amyl | 1 | 1 |
| p-2-68 | n-octyl | n-nonyl | n-nonyl | 1 | 1 |
| p-2-69 | n-nonyl | n-nonyl | n-nonyl | 1 | 1 |
| p-2-70 | n-decyl | n-nonyl | n-nonyl | 1 | 1 |
| p-2-71 | n-undecyl | n-nonyl | n-nonyl | 1 | 1 |
| p-2-72 | 1-ethylpentyl | n-nonyl | n-nonyl | 1 | 1 |
| p-2-73 | n-octyl | n-dodecyl | n-dodecyl | 1 | 1 |
| p-2-74 | n-nonyl | n-dodecyl | n-dodecyl | 1 | 1 |
| p-2-75 | n-decyl | n-dodecyl | n-dodecyl | 1 | 1 |
| p-2-76 | n-undecyl | n-dodecyl | n-dodecyl | 1 | 1 |

TABLE 2c-continued

| Compound | R¹ | R² | R³ | a | b |
|---|---|---|---|---|---|
| p-2-77 | 1-ethylpentyl | n-dodecyl | n-dodecyl | 1 | 1 |
| p-2-78 | n-octyl | cyclohexyl | cyclohexyl | 1 | 1 |
| p-2-79 | n-nonyl | cyclohexyl | cyclohexyl | 1 | 1 |
| p-2-80 | n-decyl | cyclohexyl | cyclohexyl | 1 | 1 |
| p-2-81 | n-octyl | phenyl | phenyl | 1 | 1 |
| p-2-82 | n-nonyl | phenyl | phenyl | 1 | 1 |
| p-2-83 | n-decyl | phenyl | phenyl | 1 | 1 |
| p-2-84 | n-octyl | benzyl | benzyl | 1 | 1 |
| p-2-85 | n-nonyl | benzyl | benzyl | 1 | 1 |

TABLE 2d

| Compound | R¹ | R² | R³ | a | b |
|---|---|---|---|---|---|
| p-2-86 | n-decyl | benzyl | benzyl | 1 | 1 |
| p-2-87 | n-octyl | methyl | methyl | 2 | 2 |
| p-2-88 | n-nonyl | methyl | methyl | 2 | 2 |
| p-2-89 | n-decyl | methyl | methyl | 2 | 2 |
| p-2-90 | n-octyl | ethyl | ethyl | 2 | 2 |
| p-2-91 | n-nonyl | ethyl | ethyl | 2 | 2 |
| p-2-92 | n-decyl | ethyl | ethyl | 2 | 2 |
| p-2-93 | n-octyl | iso-propyl | iso-propyl | 2 | 2 |
| p-2-94 | n-nonyl | iso-propyl | iso-propyl | 2 | 2 |
| p-2-95 | n-decyl | iso-propyl | iso-propyl | 2 | 2 |
| p-2-96 | n-octyl | sec-butyl | sec-butyl | 2 | 2 |
| p-2-97 | n-nonyl | sec-butyl | sec-butyl | 2 | 2 |
| p-2-98 | n-decyl | sec-butyl | sec-butyl | 2 | 2 |
| p-2-99 | n-octyl | tert-butyl | tert-butyl | 2 | 2 |
| p-2-100 | n-nonyl | tert-butyl | tert-butyl | 2 | 2 |
| p-2-101 | n-decyl | tert-butyl | tert-butyl | 2 | 2 |
| p-2-102 | n-octyl | methyl | methyl | 3 | 3 |
| p-2-103 | n-nonyl | methyl | methyl | 3 | 3 |
| p-2-104 | n-decyl | methyl | methyl | 3 | 3 |
| p-2-105 | n-octyl | methyl | methyl | 1 | 0 |
| p-2-106 | n-nonyl | methyl | methyl | 1 | 0 |
| p-2-107 | n-decyl | methyl | methyl | 1 | 0 |
| p-2-108 | n-octyl | methyl | methyl | 2 | 0 |
| p-2-109 | n-nonyl | methyl | methyl | 2 | 0 |
| p-2-110 | n-decyl | methyl | methyl | 2 | 0 |
| p-2-111 | n-octyl | methyl | methyl | 2 | 1 |
| p-2-112 | n-nonyl | methyl | methyl | 2 | 1 |
| p-2-113 | n-decyl | methyl | methyl | 2 | 1 |

TABLE 3a

| Compound | R¹ | R² | R³ | a | b |
|---|---|---|---|---|---|
| p-3-1 | n-hexyl | — | — | 0 | 0 |
| p-3-2 | n-heptyl | — | — | 0 | 0 |
| p-3-3 | n-octyl | — | — | 0 | 0 |
| p-3-4 | n-nonyl | — | — | 0 | 0 |
| p-3-5 | n-decyl | — | — | 0 | 0 |
| p-3-6 | n-undecyl | — | — | 0 | 0 |
| p-3-7 | n-dodecyl | — | — | 0 | 0 |
| p-3-8 | n-tridecyl | — | — | 0 | 0 |
| p-3-9 | n-tetradecyl | — | — | 0 | 0 |
| p-3-10 | n-pentadecyl | — | — | 0 | 0 |
| p-3-11 | n-hexadecyl | — | — | 0 | 0 |
| p-3-12 | n-heptadecyl | — | — | 0 | 0 |
| p-3-13 | n-octadecyl | — | — | 0 | 0 |
| p-3-14 | n-nonadecyl | — | — | 0 | 0 |
| p-3-15 | n-icosyl | — | — | 0 | 0 |
| p-3-16 | n-eicosyl | — | — | 0 | 0 |
| p-3-17 | n-henicosyl | — | — | 0 | 0 |
| p-3-18 | n-docosyl | — | — | 0 | 0 |
| p-3-19 | n-tricosyl | — | — | 0 | 0 |
| p-3-20 | n-tetracosyl | — | — | 0 | 0 |
| p-3-21 | 1-ethylpentyl | — | — | 0 | 0 |
| p-3-22 | 2,4,4-trimethylpentyl | — | — | 0 | 0 |
| p-3-23 | 3-hexenyl | — | — | 0 | 0 |
| p-3-24 | 9-decenyl | — | — | 0 | 0 |
| p-3-25 | 10-pentadecyl | — | — | 0 | 0 |
| p-3-26 | 1-ethyl-1-pentenyl | — | — | 0 | 0 |

TABLE 3a-continued

| Compound | R¹ | R² | R³ | a | b |
|---|---|---|---|---|---|
| p-3-27 | 1,5-dimethyl-4-hexenyl | — | — | 0 | 0 |
| p-3-28 | 2,6-dimethyl-5-heptenyl | — | — | 0 | 0 |
| p-3-29 | cyclohexyl | — | — | 0 | 0 |

TABLE 3b

| Compound | R¹ | R² | R³ | a | b |
|---|---|---|---|---|---|
| p-3-30 | 3-cyclohexenyl | — | — | 0 | 0 |
| p-3-31 | n-hexyl | methyl | methyl | 1 | 1 |
| p-3-32 | n-octyl | methyl | methyl | 1 | 1 |
| p-3-33 | n-nonyl | methyl | methyl | 1 | 1 |
| p-3-34 | n-decyl | methyl | methyl | 1 | 1 |
| p-3-35 | n-undecyl | methyl | methyl | 1 | 1 |
| p-3-36 | n-dodecyl | methyl | methyl | 1 | 1 |
| p-3-37 | 1-ethylpentyl | methyl | methyl | 1 | 1 |
| p-3-38 | n-octyl | ethyl | ethyl | 1 | 1 |
| p-3-39 | n-nonyl | ethyl | ethyl | 1 | 1 |
| p-3-40 | n-decyl | ethyl | ethyl | 1 | 1 |
| p-3-41 | n-undecyl | ethyl | ethyl | 1 | 1 |
| p-3-42 | 1-ethylpentyl | ethyl | ethyl | 1 | 1 |
| p-3-43 | n-octyl | iso-propyl | iso-propyl | 1 | 1 |
| p-3-44 | n-nonyl | iso-propyl | iso-propyl | 1 | 1 |
| p-3-45 | n-decyl | iso-propyl | iso-propyl | 1 | 1 |
| p-3-46 | n-undecyl | iso-propyl | iso-propyl | 1 | 1 |
| p-3-47 | 1-ethylpentyl | iso-propyl | iso-propyl | 1 | 1 |
| p-3-48 | n-octyl | allyl | allyl | 1 | 1 |
| p-3-49 | n-nonyl | allyl | allyl | 1 | 1 |
| p-3-50 | n-decyl | allyl | allyl | 1 | 1 |
| p-3-51 | n-undecyl | allyl | allyl | 1 | 1 |
| p-3-52 | 1-ethylpentyl | allyl | allyl | 1 | 1 |
| p-3-53 | n-octyl | sec-butyl | sec-butyl | 1 | 1 |
| p-3-54 | n-nonyl | sec-butyl | sec-butyl | 1 | 1 |
| p-3-55 | n-decyl | sec-butyl | sec-butyl | 1 | 1 |
| p-3-56 | n-undecyl | sec-butyl | sec-butyl | 1 | 1 |
| p-3-57 | 1-ethylpentyl | sec-butyl | sec-butyl | 1 | 1 |

TABLE 3c

| Compound | R¹ | R² | R³ | a | b |
|---|---|---|---|---|---|
| p-3-58 | n-octyl | tert-butyl | tert-butyl | 1 | 1 |
| p-3-59 | n-nonyl | tert-butyl | tert-butyl | 1 | 1 |
| p-3-60 | n-decyl | tert-butyl | tert-butyl | 1 | 1 |
| p-3-61 | n-undecyl | tert-butyl | tert-butyl | 1 | 1 |
| p-3-62 | 1-ethylpentyl | tert-butyl | tert-butyl | 1 | 1 |
| p-3-63 | n-octyl | tert-amyl | tert-amyl | 1 | 1 |
| p-3-64 | n-nonyl | tert-amyl | tert-amyl | 1 | 1 |
| p-3-65 | n-decyl | tert-amyl | tert-amyl | 1 | 1 |
| p-3-66 | n-undecyl | tert-amyl | tert-amyl | 1 | 1 |
| p-3-67 | 1-ethylpentyl | tert-amyl | tert-amyl | 1 | 1 |
| p-3-68 | n-octyl | n-nonyl | n-nonyl | 1 | 1 |
| p-3-69 | n-nonyl | n-nonyl | n-nonyl | 1 | 1 |
| p-3-70 | n-decyl | n-nonyl | n-nonyl | 1 | 1 |
| p-3-71 | n-undecyl | n-nonyl | n-nonyl | 1 | 1 |
| p-3-72 | 1-ethylpentyl | n-nonyl | n-nonyl | i | i |
| p-3-73 | n-octyl | n-dodecyl | n-dodecyl | 1 | 1 |
| p-3-74 | n-nonyl | n-dodecyl | n-dodecyl | 1 | 1 |
| p-3-75 | n-decyl | n-dodecyl | n-dodecyl | 1 | 1 |
| p-3-76 | n-undecyl | n-dodecyl | n-dodecyl | 1 | 1 |
| p-3-77 | 1-ethylpentyl | n-dodecyl | n-dodecyl | 1 | 1 |
| p-3-78 | n-octyl | cyclohexyl | cyclohexyl | 1 | 1 |
| p-3-79 | n-nonyl | cyclohexyl | cyclohexyl | 1 | 1 |
| p-3-80 | n-decyl | cyclohexyl | cyclohexyl | 1 | 1 |
| p-3-81 | n-octyl | phenyl | phenyl | 1 | 1 |
| p-3-82 | n-nonyl | phenyl | phenyl | 1 | 1 |
| p-3-83 | n-decyl | phenyl | phenyl | 1 | 1 |
| p-3-84 | n-octyl | benzyl | benzyl | 1 | 1 |
| p-3-85 | n-nonyl | benzyl | benzyl | 1 | 1 |

TABLE 3d

| Compound | R¹ | R² | R³ | a | b |
|---|---|---|---|---|---|
| p-3-86 | n-decyl | benzyl | benzyl | 1 | 1 |
| p-3-87 | n-octyl | methyl | methyl | 2 | 2 |
| p-3-88 | n-nonyl | methyl | methyl | 2 | 2 |
| p-3-89 | n-decyl | methyl | methyl | 2 | 2 |
| p-3-90 | n-octyl | ethyl | ethyl | 2 | 2 |
| p-3-91 | n-nonyl | ethyl | ethyl | 2 | 2 |
| p-3-92 | n-decyl | ethyl | ethyl | 2 | 2 |
| p-3-93 | n-octyl | iso-propyl | iso-propyl | 2 | 2 |
| p-3-94 | n-nonyl | iso-propyl | iso-propyl | 2 | 2 |
| p-3-95 | n-decyl | iso-propyl | iso-propyl | 2 | 2 |
| p-3-96 | n-octyl | sec-butyl | sec-butyl | 2 | 2 |
| p-3-97 | n-nonyl | sec-butyl | sec-butyl | 2 | 2 |
| p-3-98 | n-decyl | sec-butyl | sec-butyl | 2 | 2 |
| p-3-99 | n-octyl | tert-butyl | tert-butyl | 2 | 2 |
| p-3-100 | n-nonyl | tert-butyl | tert-butyl | 2 | 2 |
| p-3-101 | n-decyl | tert-butyl | tert-butyl | 2 | 2 |
| p-3-102 | n-octyl | methyl | methyl | 3 | 3 |
| p-3-103 | n-nonyl | methyl | methyl | 3 | 3 |
| p-3-104 | n-decyl | methyl | methyl | 3 | 3 |
| p-3-105 | n-octyl | methyl | methyl | 1 | 0 |
| p-3-106 | n-nonyl | methyl | methyl | 1 | 0 |
| p-3-107 | n-decyl | methyl | methyl | 1 | 0 |
| p-3-108 | n-octyl | methyl | methyl | 2 | 0 |
| p-3-109 | n-nonyl | methyl | methyl | 2 | 0 |
| p-3-110 | n-decyl | methyl | methyl | 2 | 0 |
| p-3-111 | n-octyl | methyl | methyl | 2 | 1 |
| p-3-112 | n-nonyl | methyl | methyl | 2 | 1 |
| p-3-113 | n-decyl | methyl | methyl | 2 | 1 |

Among the bisphenol compounds constituting the bisphenol compound (A) according to the present invention, the bisphenol compound (a2) and the bisphenol compound (a3) are not preferred. This is because, when the polyhydric phenol compound is used as a raw material for a resin, incorporation of any of the bisphenol compounds (a2) and (a3) in the polyhydric phenol compound causes the resulting resin to have an inferior thermal stability and color, as compared to incorporating the bisphenol compound (a1).

In view of the above, the ratio of the amount of the bisphenol compound (a2) with respect to the total amount of the bisphenol compound (a1) and the bisphenol compound (a2), in terms of absorption intensity ratio at 254 nm, is preferably less than 1.5% by area, more preferably 1% by area or less, still more preferably 0.5% by area or less, particularly preferably 0.3% by area or less, and most preferably 0% by area (namely, n.d.).

Likewise, the ratio of the amount of the bisphenol compound (a3) with respect to the total amount of the bisphenol compound (a1) and the bisphenol compound (a3), in terms of absorption intensity ratio at 254 nm, is preferably less than 1.5% by area, more preferably 1% by area or less, still more preferably 0.5% by area or less, particularly preferably 0.3% by area or less, and most preferably 0% by area (namely, n.d.).

In view of the above, the bisphenol compound (A) to be contained in the polyhydric phenol compound according to the present invention, in particular, is preferably:

1,1-bis(4-hydroxyphenyl)octane (the compound shown in Table 1a as "p-1-2"), 1,1-bis(4-hydroxyphenyl)nonane (the compound shown in Table 1a as "p-1-3"), 1,1-bis(4-hydroxyphenyl)decane (the compound shown in Table 1a as "p-1-4"), 1,1-bis(4-hydroxyphenyl)undecane (the compound shown in Table 1a as "p-1-5"), 1,1-bis(4-hydroxyphenyl)dodecane (the compound shown in Table 1a as "p-1-6"), 1,1-bis(4-hydroxyphenyl)tridecane (the compound shown in Table 1a as "p-1-7"), 1,1-bis(4-hydroxyphenyl)tetradecane (the compound shown in Table 1a as "p-1-8"), 1,1-bis(4-hydroxyphenyl)pentadecane (the compound shown in Table 1a as "p-1-9"), 1,1-bis(4-hydroxyphenyl)hexadecane (the compound shown in Table 1a as "p-1-10"), 1,1-bis(4-hydroxyphenyl)heptadecane (the compound shown in Table 1a as "p-1-11"), 1,1-bis(4-hydroxyphenyl)octadecane (the compound shown in Table 1a as "p-1-12"), or 1,1-bis(4-hydroxyphenyl)nonadecane (the compound shown in Table 1a as "p-1-13"); and more preferably;

1,1-bis(4-hydroxyphenyl)undecane, 1,1-bis(4-hydroxyphenyl)dodecane, 1,1-bis(4-hydroxyphenyl)tridecane, or 1,1-bis(4-hydroxyphenyl)tetradecane.

The trisphenol compound (B) (hereinafter, sometimes referred to as the "trisphenol compound (B) according to the present invention") contained in the polyhydric phenol compound according to the present invention is specifically, and preferably, any one of, or a mixture of a plurality of, trisphenol compounds represented by the following Formulae (6) to (14). The composition ratio(s) of any one of, or a plurality of the trisphenol compounds represented by the following Formulae (6) to (14) contained in the polyhydric phenol compound according to the present invention vary(ies) depending on the types of $R^4$, $R^5$ and $R^6$, the values of c, d and e, and the type of production process of the polyhydric phenol compound in the present invention. However, if the content of the trisphenol compound (B) according to the present invention, as the total composition ratio of the respective trisphenol compounds, in the polyhydric phenol compound according to the present invention is less than the above described upper limit value, it is possible to produce a resin having good physical properties, when the polyhydric phenol compound is used as a resin raw material for a polycarbonate resin or the like.

[Chem. 9]

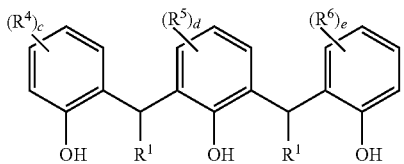

(6)

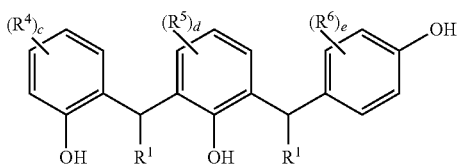

(7)

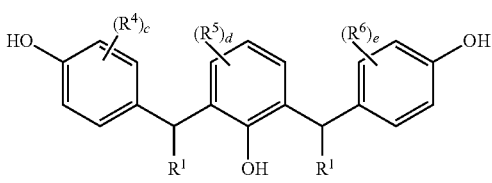

(8)

-continued

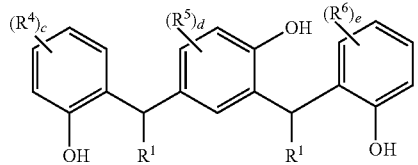

(9)

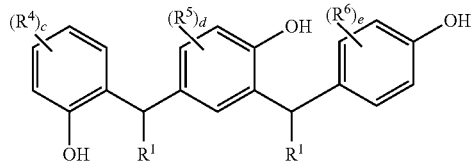

(10)

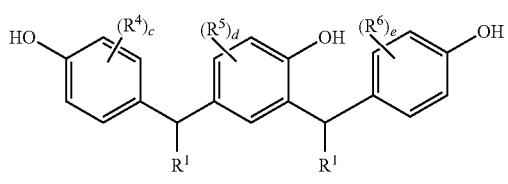

(11)

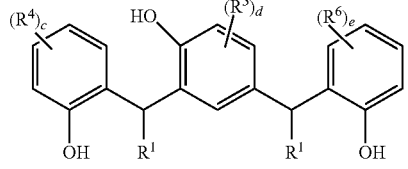

(12)

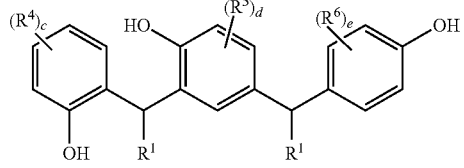

(13)

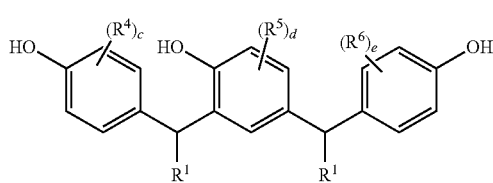

(14)

In Formulae (6) to (14), $R^1$, $R^4$, $R^5$, $R^6$, c, d and e are the same as defined in the Formula (2).

Examples of $R^1$, $R^4$, $R^5$, $R^6$, e, d and e in the trisphenol compounds (B) represented by the Formulae (6) to (14) include the combinations shown in the following Tables 4a to 4d.

TABLE 4a

| Compound | $R^1$ | $R^4$ | $R^5$ | $R^6$ | c | d | e |
|---|---|---|---|---|---|---|---|
| q-1 | n-hexyl | — | — | — | 0 | 0 | 0 |
| q-2 | n-heptyl | — | — | — | 0 | 0 | 0 |
| q-3 | n-octyl | — | — | — | 0 | 0 | 0 |
| q-4 | n-nonyl | — | — | — | 0 | 0 | 0 |
| q-5 | n-decyl | — | — | — | 0 | 0 | 0 |
| q-6 | n-undecyl | — | — | — | 0 | 0 | 0 |
| q-7 | n-dodecyl | — | — | — | 0 | 0 | 0 |
| q-8 | n-tridecyl | — | — | — | 0 | 0 | 0 |
| q-9 | n-tetradecyl | — | — | — | 0 | 0 | 0 |
| q-10 | n-pentadecyl | — | — | — | 0 | 0 | 0 |
| q-11 | n-hexadecyl | — | — | — | 0 | 0 | 0 |

TABLE 4a-continued

| Compound | $R^1$ | $R^4$ | $R^5$ | $R^6$ | c | d | e |
|---|---|---|---|---|---|---|---|
| q-12 | n-heptadecyl | — | — | — | 0 | 0 | 0 |
| q-13 | n-octadecyl | — | — | — | 0 | 0 | 0 |
| q-14 | n-nonadecyl | — | — | — | 0 | 0 | 0 |
| q-15 | n-icosyl | — | — | — | 0 | 0 | 0 |
| q-16 | n-eicosyl | — | — | — | 0 | 0 | 0 |
| q-17 | n-henicosyl | — | — | — | 0 | 0 | 0 |
| q-18 | n-docosyl | — | — | — | 0 | 0 | 0 |
| q-19 | n-tricosyl | — | — | — | 0 | 0 | 0 |
| q-20 | n-tetracosyl | — | — | — | 0 | 0 | 0 |
| q-21 | 1-ethylpentyl | — | — | — | 0 | 0 | 0 |
| q-22 | 2,4,4-trimethylpentyl | — | — | — | 0 | 0 | 0 |
| q-23 | 3-hexenyl | — | — | — | 0 | 0 | 0 |
| q-24 | 9-decenyl | — | — | — | 0 | 0 | 0 |
| q-25 | 10-pentadecyl | — | — | — | 0 | 0 | 0 |
| q-26 | 1-ethyl-1-pentenyl | — | — | — | 0 | 0 | 0 |
| q-27 | 1,5-dimethyl-4-hexenyl | — | — | — | 0 | 0 | 0 |
| q-28 | 2,6-dimethyl-5-heptenyl | — | — | — | 0 | 0 | 0 |
| q-29 | cyclohexyl | — | — | — | 0 | 0 | 0 |

TABLE 4b

| Compound | $R^1$ | $R^4$ | $R^5$ | $R^6$ | c | d | e |
|---|---|---|---|---|---|---|---|
| q-30 | 3-cyclohexenyl | — | — | — | 0 | 0 | 0 |
| q-31 | n-hexyl | methyl | methyl | methyl | 1 | 1 | 1 |
| q-32 | n-octyl | methyl | methyl | methyl | 1 | 1 | 1 |
| q-33 | n-nonyl | methyl | methyl | methyl | 1 | 1 | 1 |
| q-34 | n-decyl | methyl | methyl | methyl | 1 | 1 | 1 |
| q-35 | n-undecyl | methyl | methyl | methyl | 1 | 1 | 1 |
| q-36 | n-dodecyl | methyl | methyl | methyl | 1 | 1 | 1 |
| q-37 | 1-ethylpentyl | methyl | methyl | methyl | 1 | 1 | 1 |
| q-38 | n-octyl | ethyl | ethyl | ethyl | 1 | 1 | 1 |
| q-39 | n-nonyl | ethyl | ethyl | ethyl | 1 | 1 | 1 |
| q-40 | n-decyl | ethyl | ethyl | ethyl | 1 | 1 | 1 |
| q-41 | n-undecyl | ethyl | ethyl | ethyl | 1 | 1 | 1 |
| q-42 | 1-ethylpentyl | ethyl | ethyl | ethyl | 1 | 1 | 1 |
| q-43 | n-octyl | iso-propyl | iso-propyl | iso-propyl | 1 | 1 | 1 |
| q-44 | n-nonyl | iso-propyl | iso-propyl | iso-propyl | 1 | 1 | 1 |
| q-45 | n-decyl | iso-propyl | iso-propyl | iso-propyl | 1 | 1 | 1 |
| q-46 | n-undecyl | iso-propyl | iso-propyl | iso-propyl | 1 | 1 | 1 |
| q-47 | 1-ethylpentyl | iso-propyl | iso-propyl | iso-propyl | 1 | 1 | 1 |
| q-48 | n-octyl | allyl | allyl | allyl | 1 | 1 | 1 |
| q-49 | n-nonyl | allyl | allyl | allyl | 1 | 1 | 1 |
| q-50 | n-decyl | allyl | allyl | allyl | 1 | 1 | 1 |
| q-51 | n-undecyl | allyl | allyl | allyl | 1 | 1 | 1 |
| q-52 | 1-ethylpentyl | allyl | allyl | allyl | 1 | 1 | 1 |
| q-53 | n-octyl | sec-butyl | sec-butyl | sec-butyl | 1 | 1 | 1 |
| q-54 | n-nonyl | sec-butyl | sec-butyl | sec-butyl | 1 | 1 | 1 |
| q-55 | n-decyl | sec-butyl | sec-butyl | sec-butyl | 1 | 1 | 1 |
| q-56 | n-undecyl | sec-butyl | sec-butyl | sec-butyl | 1 | 1 | 1 |
| q-57 | 1-ethylpentyl | sec-butyl | sec-butyl | sec-butyl | 1 | 1 | 1 |

TABLE 4c

| Compound | $R^1$ | $R^4$ | $R^5$ | $R^6$ | c | d | e |
|---|---|---|---|---|---|---|---|
| q-58 | n-octyl | tert-butyl | tert-butyl | tert-butyl | 1 | 1 | 1 |
| q-59 | n-nonyl | tert-butyl | tert-butyl | tert-butyl | 1 | 1 | 1 |
| q-60 | n-decyl | tert-butyl | tert-butyl | tert-butyl | 1 | 1 | 1 |
| q-61 | n-undecyl | tert-butyl | tert-butyl | tert-butyl | 1 | 1 | 1 |
| q-62 | 1-ethylpentyl | tert-butyl | tert-butyl | tert-butyl | 1 | 1 | 1 |
| q-63 | n-octyl | tert-amyl | tert-amyl | tert-amyl | 1 | 1 | 1 |
| q-64 | n-nonyl | tert-amyl | tert-amyl | tert-amyl | 1 | 1 | 1 |
| q-65 | n-decyl | tert-amyl | tert-amyl | tert-amyl | 1 | 1 | 1 |
| q-66 | n-undecyl | tert-amyl | tert-amyl | tert-amyl | 1 | 1 | 1 |
| q-67 | 1-ethylpentyl | tert-amyl | tert-amyl | tert-amyl | 1 | 1 | 1 |
| q-68 | n-octyl | n-nonyl | n-nonyl | n-nonyl | 1 | 1 | 1 |
| q-69 | n-nonyl | n-nonyl | n-nonyl | n-nonyl | 1 | 1 | 1 |
| q-70 | n-decyl | n-nonyl | n-nonyl | n-nonyl | 1 | 1 | 1 |
| q-71 | n-undecyl | n-nonyl | n-nonyl | n-nonyl | 1 | 1 | 1 |
| q-72 | 1-ethylpentyl | n-nonyl | n-nonyl | n-nonyl | 1 | 1 | 1 |
| q-73 | n-octyl | n-dodecyl | n-dodecyl | n-dodecyl | 1 | 1 | 1 |
| q-74 | n-nonyl | n-dodecyl | n-dodecyl | n-dodecyl | 1 | 1 | 1 |
| q-75 | n-decyl | n-dodecyl | n-dodecyl | n-dodecyl | 1 | 1 | 1 |
| q-76 | n-undecyl | n-dodecyl | n-dodecyl | n-dodecyl | 1 | 1 | 1 |
| q-77 | 1-ethylpentyl | n-dodecyl | n-dodecyl | n-dodecyl | 1 | 1 | 1 |
| q-78 | n-octyl | cyclohexyl | cyclohexyl | cyclohexyl | 1 | 1 | 1 |
| q-79 | n-nonyl | cyclohexyl | cyclohexyl | cyclohexyl | 1 | 1 | 1 |
| q-80 | n-decyl | cyclohexyl | cyclohexyl | cyclohexyl | 1 | 1 | 1 |
| q-81 | n-octyl | phenyl | phenyl | phenyl | 1 | 1 | 1 |
| q-82 | n-nonyl | phenyl | phenyl | phenyl | 1 | 1 | 1 |
| q-83 | n-decyl | phenyl | phenyl | phenyl | 1 | 1 | 1 |
| q-84 | n-octyl | benzyl | benzyl | benzyl | 1 | 1 | 1 |
| q-85 | n-nonyl | benzyl | benzyl | benzyl | 1 | 1 | 1 |

TABLE 4d

| Compound | $R^1$ | $R^4$ | $R^5$ | $R^6$ | c | d | e |
|---|---|---|---|---|---|---|---|
| q-86 | n-decyl | benzyl | benzyl | benzyl | 1 | 1 | 1 |
| q-87 | n-octyl | methyl | methyl | methyl | 2 | 2 | 2 |
| q-88 | n-nonyl | methyl | methyl | methyl | 2 | 2 | 2 |
| q-89 | n-decyl | methyl | methyl | methyl | 2 | 2 | 2 |
| q-90 | n-octyl | ethyl | ethyl | ethyl | 2 | 2 | 2 |
| q-91 | n-nonyl | ethyl | ethyl | ethyl | 2 | 2 | 2 |
| q-92 | n-decyl | ethyl | ethyl | ethyl | 2 | 2 | 2 |
| q-93 | n-octyl | iso-propyl | iso-propyl | iso-propyl | 2 | 2 | 2 |
| q-94 | n-nonyl | iso-propyl | iso-propyl | iso-propyl | 2 | 2 | 2 |
| q-95 | n-decyl | iso-propyl | iso-propyl | iso-propyl | 2 | 2 | 2 |
| q-96 | n-octyl | sec-butyl | sec-butyl | sec-butyl | 2 | 2 | 2 |
| q-97 | n-nonyl | sec-butyl | sec-butyl | sec-butyl | 2 | 2 | 2 |
| q-98 | n-decyl | sec-butyl | sec-butyl | sec-butyl | 2 | 2 | 2 |
| q-99 | n-octyl | tert-butyl | tert-butyl | tert-butyl | 2 | 2 | 2 |
| q-100 | n-nonyl | tert-butyl | tert-butyl | tert-butyl | 2 | 2 | 2 |
| q-101 | n-decyl | tert-butyl | tert-butyl | tert-butyl | 2 | 2 | 2 |
| q-102 | n-octyl | methyl | methyl | methyl | 3 | 3 | 3 |
| q-103 | n-nonyl | methyl | methyl | methyl | 3 | 3 | 3 |
| q-104 | n-decyl | methyl | methyl | methyl | 3 | 3 | 3 |
| q-105 | n-octyl | methyl | methyl | methyl | 1 | 0 | 0 |
| q-106 | n-nonyl | methyl | methyl | methyl | 1 | 0 | 0 |
| q-107 | n-decyl | methyl | methyl | methyl | 1 | 0 | 0 |
| q-108 | n-octyl | methyl | methyl | methyl | 2 | 0 | 0 |
| q-109 | n-nonyl | methyl | methyl | methyl | 2 | 0 | 0 |
| q-110 | n-decyl | methyl | methyl | methyl | 2 | 0 | 0 |

TABLE 4d-continued

| Compound | $R^1$ | $R^4$ | $R^5$ | $R^6$ | c | d | e |
|---|---|---|---|---|---|---|---|
| q-111 | n-octyl | methyl | methyl | methyl | 2 | 1 | 1 |
| q-112 | n-nonyl | methyl | methyl | methyl | 2 | 1 | 1 |
| q-113 | n-decyl | methyl | methyl | methyl | 2 | 1 | 1 |

[Method of Producing Polyhydric Phenol Compound]

The method of producing the polyhydric phenol compound according to the present invention is not particularly limited, and a known method can be used. The polyhydric phenol compound according to the present invention can be easily produced, for example by: condensation of a corresponding aldehyde, acetal, thioacetal, trioxane or the like with a phenol compound in the presence of an acid catalyst.

In particular, the polyhydric phenol compound is preferably produced by a method in which an aldehyde compound represented by the following Formula (15) is allowed to react with a monophenol compound represented by the following Formula (16), because the method provides a shorter route of synthesis, decreases the amount of by-product generated, and in addition, allows for a simplified purification step and a decreased amount of waste, as a result of the by-product being water.

In other words, when the polyhydric phenol compound according to the present invention is produced by a conventionally known method, as described above, it is possible to produce a polyhydric phenol compound in which the trisphenol compound (B) according to the present invention is contained at a predetermined ratio with respect to the amount of the bisphenol compound (A) according to the present invention, by controlling reaction conditions (such as the molar ratio of the monophenol compound to the aldehyde compound, reaction temperature, the type and the amount of the catalyst used, etc.), or alternatively, by subjecting the reaction mixture obtained by the reaction to a purification treatment such as suspension washing or crystallization, so as to preferentially remove the trisphenol compound (B) according to the present invention.

[Chem. 10]

(15)

In Formula (15), $R^1$ is the same as defined in the Formula (1).

[Chem. 11]

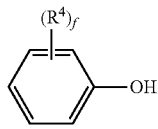

(16)

In Formula (16), $R^4$ is the same as defined in the Formula (2), and f represents an integer from 0 to 4.

<Aldehyde Compound>

Specific examples of the aldehyde compound represented by the Formula (15) include: a linear alkyl aldehyde; a branched alkyl aldehyde; an alkyl aldehyde having a partially cyclic structure; and an aldehyde in which the aliphatic hydrocarbon group represented by $R^1$ contains an unsaturated bond, such as, for example, an alkenyl aldehyde.

Specific examples of the linear alkyl aldehyde include n-heptanal, n-octanal, n-nonanal, n-decanal, n-undecanal, n-dodecanal, n-tridecanal, n-tetradecanal, n-pentadecanal, n-hexadecanal, n-heptadecanal, n-octadecanal, n-nonadecanal, n-nonadecyl aldehyde, n-icosyl aldehyde, n-henicosyl aldehyde, n-docosyl aldehyde, n-tricosyl aldehyde and n-tetracosyl aldehyde. Among these, the linear alkyl aldehyde is preferably a linear alkyl aldehyde having from 9 to 18 carbon atoms, such as n-nonanal, n-decanal, n-undecanal, n-dodecanal, n-hexadecanal or n-octadecanal, more preferably n-undecanal or n-dodecanal, and particularly preferably n-dodecanal.

Specific examples of the branched alkyl aldehyde include: methylpentyl aldehyde, methylhexyl aldehyde, methylheptyl aldehyde, methyloctyl aldehyde, methylnonyl aldehyde, methyldecyl aldehyde, methylundecyl aldehyde, methyldodecyl aldehyde, methyltridecyl aldehyde, methyltetradecyl aldehyde, methylpentadecyl aldehyde, methylhexadecyl aldehyde, methylheptadecyl aldehyde, methyloctadecyl aldehyde, methylnonadecyl aldehyde, methylicosyl aldehyde, methylicosyl aldehyde, methylhenicosyl aldehyde, methyldocosyl aldehyde and methyltricosyl aldehyde;

dimethylbutyl aldehyde, dimethylpentyl aldehyde, dimethylhexyl aldehyde, dimethylheptyl aldehyde, dimethyloctyl aldehyde, dimethylnonyl aldehyde, dimethyldecyl aldehyde, dimethylundecyl aldehyde, dimethyldodecyl aldehyde, dimethyltridecyl aldehyde, dimethyltetradecyl aldehyde, dimethylpentadecyl aldehyde, dimethylhexadecyl aldehyde, dimethylheptadecyl aldehyde, dimethyloctadecyl aldehyde, dimethylnonadecyl aldehyde, dimethylicosyl aldehyde, dimethylicosyl aldehyde, dimethylhenicosyl aldehyde and dimethyldocosyl aldehyde;

trimethylhexyl aldehyde, trimethylheptyl aldehyde, trimethyloctyl aldehyde, trimethylnonyl aldehyde, trimethyldecyl aldehyde, trimethylundecyl aldehyde, trimethyldodecyl aldehyde, trimethyltridecyl aldehyde, trimethyltetradecyl aldehyde, trimethylpentadecyl aldehyde, trimethylhexadecyl aldehyde, trimethylheptadecyl aldehyde, trimethyloctadecyl aldehyde, trimethylnonadecyl aldehyde, trimethylicosyl aldehyde, trimethylicosyl aldehyde and trimethylhenicosyl aldehyde;

ethylpentyl aldehyde, ethylhexyl aldehyde, ethylheptyl aldehyde, ethyloctyl aldehyde, ethylnonyl aldehyde, ethyldecyl aldehyde, ethylundecyl aldehyde, ethyldodecyl aldehyde, ethyltridecyl aldehyde, ethyltetradecyl aldehyde, ethylpentadecyl aldehyde, ethylhexadecyl aldehyde, ethylheptadecyl aldehyde, ethyloctadecyl aldehyde, ethylnonadecyl aldehyde, ethylicosyl aldehyde, ethylicosyl aldehyde, ethylhenicosyl aldehyde and ethyldocosyl aldehyde;

propylhexyl aldehyde, propylheptyl aldehyde, propyloctyl aldehyde, propylnonyl aldehyde, propyldecyl aldehyde, propylundecyl aldehyde, propyldodecyl aldehyde, propyltridecyl aldehyde, propyltetradecyl aldehyde, propylpentadecyl aldehyde, propylhexadecyl aldehyde, propylheptadecyl aldehyde, propyloctadecyl aldehyde, propylnonadecyl aldehyde, propylicosyl aldehyde, propylicosyl aldehyde and propylhenicosyl aldehyde; and butylhexyl aldehyde, butylheptyl aldehyde, butyloctyl aldehyde, butylnonyl aldehyde, butyldecyl aldehyde, butylundecyl aldehyde, butyldodecyl aldehyde, butyltridecyl aldehyde, butyltetradecyl aldehyde, butylpentadecyl aldehyde, butylhexadecyl aldehyde, butylheptadecyl aldehyde, butyloctadecyl aldehyde, butylnonadecyl aldehyde, butylicosyl aldehyde and butylicosyl aldehyde.

Among these, the branched alkyl aldehyde is preferably a branched alkyl aldehyde having from 8 to 18 carbon atoms, such as ethylpentyl aldehyde, ethylhexyl aldehyde, ethylheptyl aldehyde, ethyloctyl aldehyde, ethylundecyl aldehyde or ethylpentadecyl aldehyde, more preferably ethylpentyl aldehyde or ethylhexyl aldehyde, and particularly preferably ethylpentyl aldehyde.

It is to be noted that, in the above described examples of the branched alkyl aldehyde, the position of the branching is arbitrary.

Specific examples of the alkyl aldehyde having a partially cyclic structure include:

formylcyclohexane, formylcycloheptane, formylcyclooctane, formylcyclononane, formylcyclodecane, formylcycloundecane and formylcyclododecane;

formylmethylcyclohexane, formylmethylcycloheptane, formylmethylcyclooctane, formylmethylcyclononane, formylmethylcyclodecane, formylmethylcycloundecane and formylmethylcyclododecane;

formyldimethylcyclohexane, formyldimethylcycloheptane, formyldimethylcyclooctane, formyldimethylcyclononane, formyldimethylcyclodecane, formyldimethylcycloundecane and formyldimethylcyclododecane;

formylethylcyclohexane, formylethylcycloheptane, formylethylcyclooctane, formylethylcyclononane, formylethylcyclodecane, formylethylcycloundecane and formylethylcyclododecane;

formyldiethylcyclohexane, formyldiethylcycloheptane, formyldiethylcyclooctane, formyldiethylcyclononane, formyldiethylcyclodecane, formyldiethylcycloundecane and formyldiethylcyclododecane; and formylpropylcyclohexane, formylpropylcycloheptane, formylpropylcyclooctane, formylpropylcyclononane, formylpropylcyclodecane, formylpropylcycloundecane, formylpropylcyclododecane and formylcyclohexylcyclohexane.

Among these, the alkyl aldehyde having a partially cyclic structure is preferably a cyclic alkyl aldehyde having from 7 to 11 carbon atoms, such as formylcyclohexane, formylcycloheptane, formylcyclooctane, formylcyclononane, formylcyclodecane, formylmethylcyclohexane, formylmethylcycloheptane, formylmethylcyclooctane, formyldimethylcyclohexane, formyldimethylcycloheptane, formylethylcyclohexane or formylethylcycloheptane, more preferably formylcyclohexane, formylcycloheptane or formylcyclooctane, and particularly preferably formylcyclohexane.

It is to be noted that, in the above described examples of the cyclic alkyl aldehyde, the position of the substitution of the formyl group is arbitrary.

The aldehyde containing an unsaturated bond is not particularly limited, as long as it is any of the linear alkyl aldehyde, the branched alkyl aldehyde, and the alkyl aldehyde having a partially cyclic structure, as described above, which contains one or more carbon-carbon double bonds in its structure. Specific examples thereof include n-hexenyl aldehyde, n-heptynyl aldehyde, n-octenyl aldehyde, n-nonenyl aldehyde, n-decenyl aldehyde, n-undecenyl aldehyde, n-dodecenyl aldehyde, n-tridecenyl aldehyde, n-tetradecenyl aldehyde, n-pentadecenyl aldehyde, n-hexadecenyl aldehyde, n-heptadecenyl aldehyde, n-octadecenyl aldehyde, n-nonadecenyl aldehyde, n-icosenyl aldehyde, n-henicosenyl aldehyde, n-docosenyl aldehyde, n-tricosenyl aldehyde, n-tetracosenyl aldehyde, 4,8,12-trimethyltridecyl aldehyde and norbornene carboxaldehyde.

It is to be noted that, in the above described examples of the aldehyde containing an unsaturated bond, the position of the unsaturated bond is arbitrary.

<Monophenol Compound>

Specific examples of the monophenol compound represented by the Formula (16) include phenol, o-cresol, m-cresol, 2,3-dimethylphenol, 2,5-dimethylphenol, 2,6-dimethylphenol, 2-ethylphenol, 2-ethyl-6-methylphenol, 2-allylphenol, 2-isopropylphenol, 2-propylphenol, 2,3,6-trimethylphenol, 5,6,7,8-tetrahydro-1-naphthol, 2-sec-butylphenol, 2-tert-butylphenol, carvacrol, thymol, 2-tert-amylphenol, 6-tert-butyl-o-cresol, 2-phenylphenol, 2-cyclohexylphenol, 2-amyl-5-methylphenol, 2,6-diisopropylphenol, 2-benzylphenol and 2-cyclohexyl-5-methylphenol. Among these, the monophenol compound is preferably a monophenol compound containing a hydrocarbon group having three or less carbon atoms, such as phenol, o-cresol, 2,3-dimethylphenol, 2,5-dimethylphenol, 2,6-dimethylphenol, 2-ethylphenol, 2-ethyl-6-methylphenol, 2-isopropylphenol, 2-propylphenol or 2,3,6-trimethylphenol, more preferably phenol or o-cresol, and particularly preferably phenol.

<Acid Catalyst>

Examples of the acid catalyst to be used in the production of the polyhydric phenol compound according to the present invention include: inorganic acid catalysts such as phosphoric acid, oxalic acid, hydrochloric acid and sulfuric acid; organic acid catalysts such as acetic acid, trifluoroacetic acid, methane sulfonic acid, toluenesulfonic acid and trifluoromethane sulfonic acid; and heterogeneous acid catalysts such as solid acids and cation exchange resins. These acid catalysts are selected and used, taking into account a variety of factors, such as ease of handleability during the production process, reaction selectivity in the production, yield, and cost.

<Third Component>

When producing the polyhydric phenol compound according to the present invention, a third component may be incorporated into the reaction system, in order to activate the condensation reaction, and the like. Specific examples of the third component for the above described activation include: quaternary ammonium salts such as tetraethylammonium bromide, tetrabutylammonium hydrosulfate and tetrabutylammonium chloride; and sulfur-containing compounds such as ethanethiol, butanethiol, octanethiol, dodecanethiol, mercaptoacetic acid, mercaptopropionic acid, 2-mercaptoethanol, 2-aminoethanethiol, ethyl thiolactate, thiobutyric acid, pentaerythritol tetrakis(mercaptoacetic acid), 1,4-butanediol bis(thioglycolic acid) and 2-ethylhexyl (thioglycolic acid). Among these, the use of a sulfur-containing compound as the third component is preferred, from the viewpoint of facilitating the production of the polyhydric phenol compound according to the present invention. However, from the viewpoint of simplifying the purification step of the polyhydric phenol compound according to the present invention, it is preferred that none of these third components be incorporated, since it eliminates the need for separating the third component from the polyhydric phenol compound according to the present invention. These third components may be used in a state supported on a resin or the like.

The amount of the third component to be used in the production of the polyhydric phenol compound according to the present invention is not particularly limited, as long as the polyhydric phenol compound according to the present invention can be produced efficiently. However, the third component is used in such an amount that the amount thereof is usually 0.001 times or more, preferably 0.005 times or more, and particularly preferably 0.01 times or more the amount of the aldehyde compound in molar ratio. It is preferred that the amount of the third component be equal to or higher than the above described lower limit value, because it tends to allow for an efficient production of the polyhydric phenol compound according to the present invention. Further, the third component is used in such an amount that the amount thereof is usually equal to or less, preferably 0.5 times or less, and particularly preferably 0.2 times or less the amount of the aldehyde compound in molar ratio. It is preferred that the amount of the third component be equal to or lower than the above described upper limit value, because it tends to result in a decrease in the load in the step of separating the third component after being used, in the production of the polyhydric phenol compound according to the present invention. These third components may be used alone, or as a mixture of two or more kinds thereof.

<Solvent>

In the production of the polyhydric phenol compound according to the present invention, a solvent may be used to carry out the reaction. Specific examples of the solvent include: linear hydrocarbon solvents having from 5 to 18 carbon atoms, such as n-pentane, n-hexane, n-heptane, n-octane and petroleum ether; branched hydrocarbon solvents having from 5 to 18 carbon atoms, such as isooctane; cyclic hydrocarbon solvents having from 5 to 18 carbon atoms, such as cyclohexane, cyclooctane and methylcyclohexane; water; alcohol solvents such as methanol, ethanol, isopropanol and butanol; nitrile solvents such as acetonitrile; ether solvents such as dibutyl ether; ketone solvents such as methyl ethyl ketone and methyl isobutyl ketone; ester solvents such as ethyl acetate and butyl acetate; nitrogen-containing solvents such as dimethylformamide and dimethylacetamide; sulfur-containing solvents such as dimethyl sulfoxide and sulfolane; chlorine-containing solvents such as methylene chloride, chloroform and dichloroethane; and aromatic hydrocarbon solvents such as benzene, toluene and xylene. The use of any of these solvents is preferred, from the viewpoint of improving the operability of the reaction, such as, for example, preventing the solidification of raw materials during the reaction, or preventing an unexpected side reaction due to internal heat generation. However, from the viewpoint of simplifying the purification step of the polyhydric phenol compound according to the present invention, it is preferred not to use any of these solvents, since it eliminates the need for separating the solvent from the polyhydric phenol compound according to the present invention.

<Molar Ratio of Monophenol Compound to Aldehyde Compound>

In cases where the polyhydric phenol compound according to the present invention is produced by allowing the above described aldehyde compound to react with the above described monophenol compound, the reaction mixture obtained by the reaction is usually a mixture containing as main components the bisphenol compound (A) according to the present invention and the trisphenol compound (B) according to the present invention. The composition ratio of these compounds varies depending on the reaction conditions (such as the molar ratio of the monophenol compound to the aldehyde compound, reaction temperature, the type and the amount of the catalyst used etc.). Those skilled in the art can easily carry out some preliminary tests to determine the reaction conditions, and to adjust the ratio of the trisphenol compound (B) to the bisphenol compound (A) according to the present invention to an arbitrary ratio. Further, the ratio of the trisphenol compound (B) to the bisphenol compound (A) according to the present invention can be adjusted to an arbitrary ratio, also by carrying out a purification treatment such as suspension washing or crystallization using a specific solvent, preferably, using at least one hydrocarbon solvent, after the completion of the reaction, so as to preferentially remove the trisphenol compound (B) according to the present invention.

The molar ratio of the monophenol compound to the aldehyde compound to be subjected to the reaction is such that the amount of the monophenol compound is usually equal to or more, preferably two times or more, and more preferably three times or more the amount of the aldehyde compound in molar ratio. It is preferred that the above described molar ratio be adjusted such that the amount of the monophenol compound is equal to or higher than the above described lower limit value, because it allows for further reducing the ratio of the trisphenol compound (B) with respect to the bisphenol compound (A) according to the present invention, and the ratio of the trisphenol compound (B) according to the present invention in the polyvalent phenol according to the present invention can be more easily controlled to the preferred range.

At the same time, the molar ratio of the monophenol compound to the aldehyde compound to be subjected to the reaction is such that the amount of the monophenol compound is usually 100 times or less, preferably 20 times or less, and particularly preferably 10 times or less the amount of the aldehyde compound in molar ratio. It is preferred that the above described molar ratio be adjusted such that the amount of the monophenol compound is equal to or lower than the above described upper limit value, because it tends to simplify the purification treatment.

<Reaction Temperature>

The reaction temperature is usually 0° C. or higher, preferably 15° C. or higher, and particularly preferably 30° C. or higher. A reaction temperature equal to or higher than the above described lower limit value is preferred, because the solidification of the reaction mixture tends to be more easily prevented. At the same time, the reaction temperature is usually 150° C. or lower, preferably 120° C. or lower, and particularly preferably 90° C. or lower. A reaction temperature equal to or lower than the above described upper limit value is preferred, because the ratio of the trisphenol compound (B) to the bisphenol compound (A) according to the present invention tends to be more easily controlled.

<Acid Catalyst Removal Step>

The production process of the polyhydric phenol compound according to the present invention may include the step of removing the acid catalyst used. Specific examples of the catalyst removal step include: a neutralization step in which the catalyst is neutralized with a base; a removal step in which the catalyst is removed by being dissolved in a solvent; and a removal step in which the catalyst is removed by filtration. Among the above described steps, the production process preferably includes a neutralization step with a base, in cases where an inorganic acid catalyst or an organic acid catalyst is used as the acid catalyst; and the production process preferably includes a removal step by filtration, in cases where a heterogeneous catalyst is used as the acid catalyst; because it tends to allow for an efficient removal of the acid catalyst, in both cases. These catalyst removal steps may be used alone, or in combination.

Specific examples of the base to be used in the neutralization step with a base include: inorganic bases containing an alkali-metal atom or an alkaline-earth-metal atom, such as sodium hydrogen carbonate, potassium hydrogen carbonate, sodium carbonate, potassium carbonate, cesium carbonate, sodium acetate, potassium acetate, cesium acetate, sodium hydroxide, potassium hydroxide, sodium monohydrogen phosphate, potassium monohydrogen phosphate, sodium phosphate, potassium phosphate, magnesium hydroxide, calcium hydroxide, sodium hydroxide and sodium amide; organic bases containing an alkali-metal atom or an alkaline-earth-metal atom, such as sodium citrate, potassium citrate, sodium succinate, potassium succinate, calcium succinate, sodium methoxide, potassium methoxide and potassium-tert-butoxide; and nitrogen-containing compounds, such as pyridine, aniline, triethylamine, N,N-dimethylaniline, morpholine, 1,4-diazabicyclo[2,2,2]octane and diazabicycloundecene. Among these, it is preferred to use a base containing an alkali-metal atom or an alkaline-earth-metal atom, such as sodium hydrogen carbonate, potassium hydrogen carbonate, sodium carbonate, potassium carbonate, cesium carbonate, sodium acetate, potassium acetate, cesium acetate, sodium hydroxide, potassium hydroxide, sodium monohydrogen phosphate, potassium monohydrogen phosphate, sodium phosphate, potassium phosphate, magnesium hydroxide, calcium hydroxide, sodium hydroxide, sodium citrate, potassium citrate, sodium succinate and potassium succinate, from the viewpoint of facilitating the removal of the neutralized salt. These bases may be used alone, or in combination of two or more kinds thereof.

In the neutralization step, a second component may be added in order to adjust the acidity of the reaction mixture. Specific examples of the second component include: organic acids such as acetic acid, citric acid, succinic acid and malic acid; and acids containing a hetero atom other than an oxygen atom, such as phosphoric acid, sodium dihydrogen phosphate, potassium dihydrogen phosphate, ammonium chloride and monosodium citrate. The type and the amount of the second component are variably selected depending on the type and the amount of the acid catalyst to be used in the reaction step, the type and the amount of the base to be used in the neutralization step, and the target value of the acidity of the reaction mixture after the neutralization.

The reaction mixture after the neutralization step is preferably weakly acidic to weakly basic, since the resulting polyhydric phenol compound according to the present invention tends to have an improved stability. The expression that "the reaction mixture is weakly acidic to weakly basic" means that, when water is added to the reaction mixture so as to adjust the mass ratio of water and other components to 1:3, the resulting aqueous layer has a pH of usually 2 or more, preferably 3 or more, particularly preferably 4 or more, and at the same time, a pH of usually 11 or less, preferably 10 or less, and particularly preferably 9 or less. It is preferred that the pH of the aqueous layer be within the above described range, because the stability of the polyhydric phenol compound according to the present invention tends to improve.

Specific examples of the solvent to be used in the catalyst removal step in which the catalyst is removed by being dissolved in a solvent include: water; and organic solvents such as methanol, ethanol, propanol, dimethyl sulfoxide, diethyl ether and N-methylpyrrolidone. Among these, the use of water is preferred, from the viewpoint of simplifying the purification step.

Examples of a filtering material to be used in the catalyst removal step in which the catalyst is removed by filtration include: filtering materials in the form of powder, ground state, spheres or the like, such as activated carbon, silica gel, activated white clay and diatomaceous earth; and filtering materials formed into fibers or fabrics, such as paper filters, filter cloths and yarn wound filters. These filtering materials are variably selected, taking into accounts the properties of the acid catalyst used, and whether or not the acid catalyst can be reused.

<Concentration Step>

The production process of the polyhydric phenol compound according to the present invention may include the step of removing components having a low boiling point, such as solvents and unreacted raw materials by concentration, from the reaction mixture containing the polyhydric phenol compound according to the present invention (hereinafter, sometimes referred to as the "concentration step"). By performing the concentration step, the efficiency of retrieving the polyhydric phenol compound according to the present invention in a precipitation step to be described later tends to improve. The concentration step is usually carried out under the conditions of heat and reduced pressure. The concentration step is preferably carried out at a heating temperature of 40° C. or higher, more preferably 60° C. or higher, and particularly preferably 80° C. or higher. At the same time, the heating temperature is usually 200° C. or lower, preferably 180° C. or lower, and particularly preferably 160° C. or lower. A heating temperature within the above described temperature range tends to allow for an efficient implementation of the concentration step, as well as the prevention of the decomposition of the polyhydric phenol compound according to the present invention. The "heating temperature" as used in the present concentration step refers to the temperature of a heating medium to be used for the heating. The degree of pressure reduction is usually less than 760 Torr, preferably 200 Torr or less, more preferably 100 Torr or less, and particularly preferably 50 Torr or less. A degree of pressure reduction equal to or lower than the above described upper limit value tends to allow for an efficient implementation of the concentration step. Although the lower limit value of the degree of pressure reduction is not particularly defined, it is usually 0.1 Torr or more, preferably 1 Torr or more, more preferably 10 Torr or more, and particularly preferably 20 Torr or more, since a widely and commonly used apparatus for reducing pressure can be used.

<Crude Purification Step>

In the production of the polyhydric phenol compound according to the present invention, the reaction mixture obtained by the reaction of the above described aldehyde compound and monophenol compound, followed by the subsequent step of removing the acid catalyst, or alternatively, followed by the step of removing the acid catalyst and the concentration step, is usually a mixture containing as a main component the polyhydric phenol compound according to the present invention. The production process of the polyhydric phenol compound according to the present invention preferably includes, before the precipitation step to be described later, a crude purification step in which components other than the polyhydric phenol compound according to the present invention are roughly removed from the above described reaction mixture containing as a main component the polyhydric phenol compound according to the present invention.

The crude purification step is carried out, preferably, by extracting the polyhydric phenol compound according to the present invention from the reaction mixture with an extraction solvent, and then washing the thus obtained extractant layer containing the polyhydric phenol compound according to the present invention with water, followed by removing the extraction solvent from the extractant layer under reduced pressure.

The extraction solvent to be used in the extraction is not particularly limited as long as it is a good solvent of the polyhydric phenol compound according to the present invention. Specific examples thereof include solvents which can be used in the production of the polyhydric phenol compound according to the present invention, excluding water. From the viewpoint of facilitating the extraction of the polyhydric phenol compound according to the present invention, it is preferred that at least any one solvent selected from ether solvents, ketone solvents, ester solvents, chlorine-containing solvents and aromatic hydrocarbon solvents be contained, more preferably at least any one solvent selected from ketone solvents, ester solvents and aromatic hydrocarbon solvents be contained, and particularly preferably at least any one solvent selected from aromatic hydrocarbon solvents be contained. Among these, toluene or xylene is preferably contained, and toluene is most preferably contained.

These extraction solvents may be used alone, or in combination of two or more kinds thereof.

The extraction solvent is preferably used in an amount of 0.1 times by mass or more, more preferably in an amount of 0.5 times by mass or more, and particularly preferably in an equal amount by mass or more, with respect to the amount of the reaction mixture. When the amount of the extraction solvent used is equal to or higher than the above described lower limit value, it tends to allow for an efficient extraction of the polyhydric phenol compound according to the present invention. Further, the extraction solvent is preferably used in an amount of 20 times by mass or less, more preferably in an amount of 10 times by mass or less, and particularly preferably in an amount of 5 times by mass or less, with respect to the amount of the reaction mixture. When the amount of the extraction solvent used is equal to or lower than the above described upper limit value, the production efficiency of the polyhydric phenol compound according to the present invention tends to improve.

Further, an extractant layer which is obtained by extraction and which contains the polyhydric phenol compound according to the present invention is subjected to water washing, and water for washing the extractant layer is usually used in an amount of 0.1 times by mass or more, preferably in an amount of 0.5 times by mass or more, and particularly preferably in an equal amount by mass or more, with respect to the total amount of the extractant layer. When the amount of water used is equal to or higher than the above described lower limit value, the purification efficiency in the crude purification step tends to improve. Further, the water for washing is usually used in an amount of 10 times by mass or less, preferably in an amount of 5 times by mass or less, and particularly preferably in an amount of 3 times by mass or less, with respect to the total amount of the extractant layer. When the amount of water used is equal to or lower than the above described upper limit value, the production efficiency of the polyhydric phenol compound according to the present invention tends to improve.

The number of times for carrying out the water washing of the extractant layer is usually about from 1 to 20 times, preferably from 2 to 10 times, and particularly preferably from 3 to 6 times. When the number of times of water washing is equal to or higher than the above described lower limit value, the purification efficiency in the crude purification step tends to improve; whereas when the number of times is equal to or lower than the above described upper limit value, the production efficiency of the polyhydric phenol compound according to the present invention tends to improve.

When removing the extraction solvent after the above described water washing, the removal is carried out usually at a temperature of from 40 to 200° C., and under a reduced pressure of 760 to 1 Torr. The above described temperature refers to the temperature of the heating medium used.

The present crude purification step may be carried out so as to also serve as the acid catalyst removal step and the concentration step described above.

<Precipitation Step>

The method of producing the polyhydric phenol compound according to the present invention preferably includes the step of allowing the polyhydric phenol compound according to the present invention to precipitate from the reaction mixture containing the polyhydric phenol compound according to the present invention, from the solvent containing at least one aliphatic hydrocarbon solvent (hereinafter, sometimes referred to as the "precipitation step").

The precipitation step can usually be carried out by: mixing the reaction mixture containing the polyhydric phenol compound according to the present invention and a solvent containing an aliphatic hydrocarbon solvent, followed by cooling and leaving the mixture to stand. By carrying out the precipitation step to preferentially remove the trisphenol compound (B) according to the present invention in the resulting reaction mixture obtained by the reaction, it is possible to control the ratio of the trisphenol compound (B) according to the present invention with respect to the bisphenol compound (A) according to the present invention within the range defined in the present invention.

Specific examples of the aliphatic hydrocarbon solvent to be used in the precipitation step include: linear hydrocarbon solvents having from 5 to 18 carbon atoms, such as n-pentane, n-hexane, n-heptane, n-octane and petroleum ether; branched hydrocarbon solvents having from 5 to 18 carbon atoms, such as isooctane; and cyclic hydrocarbon solvents having from 5 to 18 carbon atoms, such as cyclohexane, cyclooctane and methylcyclohexane. Among these, it is preferred to use a hydrocarbon solvent having from 6 to 10 carbon atoms, and more preferably a hydrocarbon solvent having from 6 to 8 carbon atoms, because it facilitates the removal of the solvent from the polyhydric phenol compound according to the present invention. One of these hydrocarbon solvents may be used alone, or two or more kinds thereof may be used as a mixture.

The solvent to be used in the precipitation step may contain, as a second solvent, a solvent other than the aliphatic hydrocarbon solvent. Specific examples of the second solvent include: water; alcohol solvents such as methanol, ethanol, isopropanol and butanol; nitrile solvents such as acetonitrile; ether solvents such as dibutyl ether; ketone solvents such as methyl ethyl ketone and methyl isobutyl ketone; ester solvents such as ethyl acetate and butyl acetate; nitrogen-containing solvents such as dimethylformamide and dimethylacetamide; sulfur-containing solvents such as dimethyl sulfoxide and sulfolane; chlorine-containing solvents such as methylene chloride, chloroform and dichloroethane; and aromatic hydrocarbon solvents such as benzene, toluene and xylene. Among these, it is preferred that either an alcohol solvent or an aromatic hydrocarbon solvent be contained as the second solvent, because it allows for an efficient purification of the polyhydric phenol compound according to the present invention, and enables to easily control the ratio of the trisphenol compound (B) with respect to the bisphenol compound (A) according to the present invention. One of these second solvents may be used alone, or two or more kinds thereof may be used as a mixture.

The mixing ratio of the second solvent and the aliphatic hydrocarbon solvent is not particularly limited, and can be set as appropriate as long as the properties of the polyhydric phenol compound according to the present invention are not impaired. However, the composition ratio of the aliphatic hydrocarbon solvent in the total solvent is usually from 10 to 99% by mass. It is preferred that the composition ratio of the aliphatic hydrocarbon solvent in the total solvent be equal to or lower than the above described upper limit value, because it facilitates an efficient removal of the trisphenol compound (B) according to the present invention, and enables to easily control the amount of the trisphenol compound (B) in the polyhydric phenol compound according to the present invention. At the same time, such a composition ratio is preferred, also because it facilitates an efficient removal of the bisphenol compound (a2) and the bisphenol compound (a3), and enables to easily control the purity of the bisphenol compound (a1). Further, it is preferred that the composition ratio of the aliphatic hydrocarbon solvent in the total solvent be equal to or higher than the above described lower limit value, because it enables to prevent a situation in which the bisphenol compound (A) is selectively dissolved in the second solvent and removed; namely, a decrease in the yield can be prevented. In view of the above, the composition ratio of the aliphatic hydrocarbon solvent in the total solvent is more preferably from 20 to 98% by mass, and still more preferably from 25 to 97% by mass, and particularly preferably from 30 to 96% by mass.

The mixing ratio of the reaction mixture containing the polyhydric phenol compound according to the present invention and the above described solvents is not particularly defined, as long as it allows for an efficient precipitation of the polyhydric phenol compound according to the present invention. However, in general, the mass ratio of the total solvent to the reaction mixture containing the polyhydric phenol compound according to the present invention is such that the amount of the total solvent is preferably 0.2 times or more, more preferably 0.5 times or more, and particularly preferably equal to or more the amount of the reaction mixture in mass ratio. At the same time, the above described mass ratio is such that the amount of the total solvent is preferably 100 times or less, more preferably 50 times or less, and particularly preferably 10 times or less the amount of the reaction mixture in mass ratio. It is preferred that the mass ratio be adjusted such that the amount of the total solvent is equal to or higher than the above described lower limit value, because it tends to facilitate the preferential precipitation of the reaction mixture containing the polyhydric phenol compound according to the present invention. At the same time, it is preferred that the mass ratio be adjusted such that the amount of the total solvent is equal to or lower than the above described upper limit value, because the production efficiency of the polyhydric phenol compound according to the present invention tends to improve.

When the reaction mixture containing the polyhydric phenol compound according to the present invention as a main component is mixed with the above described solvent containing at least one aliphatic hydrocarbon solvent, the aliphatic hydrocarbon solvent and the second solvent may be added to the reaction mixture separately, or these solvents may be mixed in advance, and then mixed with the reaction mixture. From the viewpoint of improving the production efficiency of the polyhydric phenol compound according to the present invention, the aliphatic hydrocarbon solvent and the second solvent are preferably mixed in advance.

In the precipitation step, the reaction mixture containing the polyhydric phenol compound according to the present invention as a main component, and the above described solvent containing at least one aliphatic hydrocarbon solvent are usually mixed at a mixing temperature of 0° C. or higher, preferably 20° C. or higher, and particularly preferably 40° C. or higher. At the same time, the mixing temperature is usually equal to or lower than the boiling point of the solvent, preferably equal to or lower than (the boiling point of the solvent −5)° C., and particularly preferably equal to or lower than (the boiling point of the solvent −10)° C. It is preferred that the mixing temperature be equal to or higher than the above described lower limit value and equal to or lower than the above described upper limit value, because it enables to efficiently dissolve the polyhydric phenol compound according to the present invention. In cases where two or more kinds of solvents are used as a mixture, the above described boiling point of the solvent refers to the boiling point of the mixed solvents.

The temperature at which the polyhydric phenol compound according to the present invention is allowed to precipitate, after the mixing, is not particularly limited, and the above described precipitation temperature can be set as appropriate, as long as the properties of the polyhydric phenol compound according to the present invention are not impaired. However, the precipitation temperature is usually −20° C. or higher, preferably −10° C. or higher, and particularly preferably 0° C. or higher. At the same time, the precipitation temperature is usually 70° C. or lower, preferably 65° C. or lower, and particularly preferably 60° C. or lower. It is preferred that the precipitation temperature be within the above described range, because it tends to allow for an efficient precipitation and purification of the polyhydric phenol compound according to the present invention.

After allowing the polyhydric phenol compound according to the present invention to precipitate in the above described precipitation step, a powder of the polyhydric phenol compound according to the present invention is collected from the solvent used, by carrying out solid-liquid separation using methods such as filtration, centrifugal separation, decantation and the like.

In the precipitation step, seed crystals of the polyhydric phenol compound according to the present invention may be added, in order to improve the precipitation efficiency of the polyhydric phenol compound according to the present invention. From the viewpoint of improving the production efficiency of the polyhydric phenol compound according to the present invention, the amount of the seed crystals to be added is usually from 0.0001 to 10%, preferably from 0.0005 to 5%, and particularly preferably from 0.001 to 1% in mass ratio, with respect to the amount of the reaction mixture containing the polyhydric phenol compound according to the present invention as a main component.

The number of times for carrying out the precipitation step is variably selected depending on the intended degree of purification of the polyhydric phenol compound according to the present invention. However, in general, the precipitation step is carried out preferably three times or less, and more preferably twice or less, and particularly preferably once, from the viewpoint of simplifying the purification treatment.

<Washing Step>

After the precipitation step, the powder of the resulting polyhydric phenol compound according to the present invention may further be washed using a solvent, in order to carry out surface washing. Specific examples of the solvent to be used in the washing include solvents described above as examples of the aliphatic hydrocarbon solvent and the second solvent. The washing step is usually carried out at a washing temperature of −20° C. or higher, preferably −10° C. or higher, and particularly preferably 0° C. or higher. At the same time, the washing temperature is usually 70° C. or lower, preferably 60° C. or lower, and particularly preferably 50° C. or lower. It is preferred that the washing temperature be within the above described range, because it tends to prevent an excessive dissolution of the polyhydric phenol compound according to the present invention in the solvent for washing.

<Solvent Removal Step>

The powder of the polyhydric phenol compound according to the present invention obtained through the above descried precipitation step and washing step, may further be subjected to a solvent removal treatment by heating, decompression, air drying and/or the like, to obtain the polyhydric phenol compound according to the present invention which substantially does not contain any solvent. The solvent removal treatment is usually carried out at a temperature of 20° C. or higher, and preferably 40° C. or higher, in order to allow the solvent removal treatment to proceed smoothly. The upper limit of the temperature is usually equal to or lower than the melting point of the polyhydric phenol compound according to the present invention, preferably 75° C. or lower, and particularly preferably 72° C. or lower.

<Grinding Step and Classification Step>

The powder of the polyhydric phenol compound according to the present invention obtained through the above descried precipitation step and washing step, or alternatively, obtained through these steps and further through the above described solvent removal step, may further be subjected to grinding, classification and the like to control the powder properties, in order to improve the handleability. The grinding can be carried out using any of various types of methods which allow for grinding powders in general, for example, by a method using a bead mill, a roll mill, a hammer mill, a planetary mill, or the like. Further, the classification can be carried out using any of various types of methods which allow for classifying powders in general, for example, by dry classification, wet classification, sieve classification, or the like.

However, from the viewpoint of reducing the load in the production of the polyhydric phenol compound according to the present invention, it is preferred not to carry out the above described grinding and classification steps.

Containing the trisphenol compound (B) in a content within the above described suitable range is also preferred from the above described view point, because the polyhydric phenol compound according to the present invention having good powder properties can be obtained without carrying out the above described grinding and classification steps.

[Use of Polyhydric Phenol Compound]

The polyhydric phenol compound according to the present invention can be used as a component of a resin, a curing agent, an additive, or a precursor thereof, which is used in various types of applications such as optical materials, recording materials, insulating materials, transparent materials, electronic materials, adhesive materials and heat-resistant materials. Examples of the resin which can be produced using the polyhydric phenol compound as a component include: various types of thermoplastic resins such as polyether resins, polyester resins, polyarylate resins, polycarbonate resins, polyurethane resins and acrylic resins; and various types of thermosetting resins such as epoxy resins, unsaturated polyester resins, phenol resins, polybenzoxazine resins and cyanate resins. Further, the polyhydric phenol compound is also useful as a color developer or an antifading agent for use in a thermosensitive recording material or the like, or as an additive such as a bactericide or an antibacterial antifungal agent.

Among these, the polyhydric phenol compound is preferably used as a raw material (monomer) for a thermoplastic resin or a thermosetting resin, because it allows for obtaining a resin having good mechanical properties. In particular, from the viewpoint of allowing the polyhydric phenol compound according to the present invention to effectively exhibit its excellent alkali resistance, the polyhydric phenol compound is more preferably used as a raw material for a resin which is produced by polymerizing a raw material monomer in the presence of an alkaline catalyst, and still more preferably used as a raw material for a polycarbonate resin or an epoxy resin. Further, the use of the polyhydric phenol compound as a color developer is also preferred, and in particular, the use thereof in combination with a leuco dye and/or a color-change temperature regulator is more preferred.

[Polycarbonate Resin]

A description will be given below regarding a polycarbonate resin (hereinafter, sometimes referred to as the "polycarbonate resin according to the present invention") which can be obtained by polymerization of the polyhydric phenol compound according to the present invention.

The "polycarbonate resin according to the present invention" refers to a polycarbonate resin in a broad sense, including a polyester carbonate, as will be described later.

The polycarbonate resin according to the present invention is produced using the polyhydric phenol compound according to the present invention, and the polycarbonate resin according to the present invention has superior mechanical properties such as flowability, impact strength and flexural strength as compared to conventionally known polycarbonate resins, and also has a good balance between the mechanical properties and optical properties.

<Other Dihydroxy Compound>

The polycarbonate resin according to the present invention may also be a polycarbonate resin copolymer obtained by polymerizing, together with the polyhydric phenol compound according to the present invention, another dihydroxy compound which is different from the bisphenol compound (A) according to the present invention contained in the polyhydric phenol compound according to the present invention, to the extent that the characteristics of the polycarbonate resin according to the present invention are not impaired. The form of the polycarbonate resin copolymer can be selected from various types of copolymerization forms, and the copolymer may be, for example, a random copolymer or a block copolymer.

In cases where another dihydroxy compound different from the bisphenol compound (A) according to the present invention is used in the production of the polycarbonate resin according to the present invention, the ratio of the amount of the other dihydroxy compound with respect to the amount of total dihydroxy compound, which is the total sum of the amounts of the bisphenol compound (A) according to the present invention and the other dihydroxy compound, may be selected as appropriate. However, the ratio is usually from 0.1 to 50% by mole.

When the ratio of the other dihydroxy compound is less than the lower limit value of the above described range, there is a possibility that the modifying effect of the other dihydroxy compound cannot not be sufficiently obtained.

When the ratio is more than the upper limit value of the above described range, on the other hand, there is a possibility that the resulting polycarbonate resin according to the present invention has an insufficient strength, heat resistance and thermal stability. In view of the above, the ratio of the other dihydroxy compound is preferably 0.5% by mole or more, more preferably 1% by mole or more, and still more preferably 1.5% by mole or more. At the same time, the ratio of the other dihydroxy compound is preferably 40% by mole or less, more preferably 35% by mole or less, still more preferably 20% by mole or less, and particularly preferably 10% by mole or less.

Those skilled in the art can easily identify the ratio of the other dihydroxy compound with respect to the total dihydroxy compound, by analyzing the respective dihydroxy compounds obtained by hydrolysis of the polycarbonate resin, using a known analysis method such as NMR.

The other dihydroxy compound described above is not particularly limited, and may be an aromatic dihydroxy compound which contains an aromatic ring within the molecular skeleton, or an aliphatic dihydroxy compound which does not contain an aromatic ring. The other dihydroxy compound may also be a dihydroxy compound into which a hetero atom(s), such as N (nitrogen), S (sulfur), P (phosphorus) and/or Si (silicon), and/or a hetero bond(s) is/are introduced in order to provide various properties.

Specific examples of the other dihydroxy compound which can be suitably used include the following:

dihydroxybenzenes such as 1,2-dihydroxybenzene, 1,3-dihydroxybenzene (namely, resorcinol) and 1,4-dihydroxybenzene;

dihydroxybiphenyls such as 2,5-dihydroxybiphenyl, 2,2'-dihydroxybiphenyl and 4,4'-dihydroxybiphenyl;

dihydroxynaphthalenes such as 2,2'-dihydroxy-1,1'-binaphthyl, 1,2-dihydroxynaphthalene, 1,3-dihydroxynaphthalene, 2,3-dihydroxynaphthalene, 1,6-dihydroxynaphthalene, 2,6-dihydroxynaphthalene, 1,7-dihydroxynaphthalene and 2,7-dihydroxynaphthalene;

dihydroxy diaryl ethers such as 2,2'-dihydroxydiphenyl ether, 3,3'-dihydroxydiphenyl ether, 4,4'-dihydroxydiphenyl ether, 4,4'-dihydroxy-3,3'-dimethyldiphenyl ether, 1,4-bis(3-hydroxyphenoxy)benzene, and 1,3-bis(4-hydroxyphenoxy)benzene.

bis(hydroxyaryl) alkanes such as 1,1-bis(4-hydroxyphenyl)propane, 2,2-bis(3-methyl-4-hydroxyphenyl)propane, 2,2-bis(3-methoxy-4-hydroxyphenyl)propane, 2-(4-hydroxyphenyl)-2-(3-methoxy-4-hydroxyphenyl)propane, 1,1-bis(3-tert-butyl-4-hydroxyphenyl)propane, 2,2-bis(3,5-dimethyl-4-hydroxyphenyl)propane, 2,2-bis(3-cyclohexyl-4-hydroxyphenyl)propane, 2-(4-hydroxyphenyl)-2-(3-cyclohexyl-4-hydroxyphenyl)propane, α,α'-bis(4-hydroxyphenyl)-1,4-diisopropylbenzene, 1,3-bis[2-(4-hydroxyphenyl)-2-propyl]benzene, 4,4-dihydroxydiphenylmethane, bis(4-hydroxyphenyl)cyclohexylmethane, bis(4-hydroxyphenyl)phenylmethane, bis(4-hydroxyphenyl)(4-propenylphenyl)methane, bis(4-hydroxyphenyl)diphenylmethane, bis(4-hydroxyphenyl)naphthylmethane, 1,1-bis(4-hydroxyphenyl)ethane, 1,1-bis(4-hydroxyphenyl)-1-phenylethane, 1,1-bis(4-hydroxyphenyl)-1-naphthylethane, 1,1-bis(4-hydroxyphenyl)butane, 2,2-bis(4-hydroxyphenyl)butane and 2,2-bis(4-hydroxyphenyl)pentane;

bis(hydroxyaryl) cycloalkanes such as 1,1-bis(4-hydroxyphenyl)cyclopentane, 1,1-bis(4-hydroxyphenyl)cyclohexane, 1,1-bis(4-hydroxyphenyl)-3,3-dimethylcyclohexane, 1,1-bis(4-hydroxyphenyl)-3,4-dimethylcyclohexane, 1,1-bis(4-hydroxyphenyl)-3,5-dimethylcyclohexane, 1,1-bis(4-hydroxyphenyl)-3,3,5-trimethylcyclohexane, 1,1-bis(4-hydroxy-3,5-dimethylphenyl)-3,3,5-trimethylcyclohexane, 1,1-bis(4-hydroxyphenyl)-3-propyl-5-methylcyclohexane, 1,1-bis(4-hydroxyphenyl)-3-tert-butyl-cyclohexane, 1,1-bis(4-hydroxyphenyl)-4-tert-butyl-cyclohexane, 1,1-bis(4-hydroxyphenyl)-3-phenylcyclohexane, and 1,1-bis(4-hydroxyphenyl)-4-phenylcyclohexane;

cardo structure-containing bisphenols such as 9,9-bis(4-hydroxyphenyl)fluorene and 9,9-bis(4-hydroxy-3-methylphenyl)fluorene;

dihydroxydiaryl sulfides such as 4,4'-dihydroxydiphenyl sulfide and 4,4'-dihydroxy-3,3'-dimethyldiphenyl sulfide;

dihydroxydiaryl sulfoxides such as 4,4'-dihydroxydiphenyl sulfoxide and 4,4'-dihydroxy-3,3'-dimethyldiphenyl sulfoxide;

dihydroxydiaryl sulfones such as 4,4'-dihydroxydiphenyl sulfone and 4,4'-dihydroxy-3,3'-dimethyldiphenyl sulfone;

alkane diols such as ethane-1,2-diol, propane-1,2-diol, propane-1,3-diol, 2,2-dimethylpropane-1,3-diol, 2-methyl-2-propylpropane-1,3-diol, butane-1,4-diol, pentane-1,5-diol, hexane-1,6-diol and decane-1,10-diol;

cycloalkane diols such as cyclopentane-1,2-diol, cyclohexane-1,2-diol, cyclohexane-1,4-diol, 1,4-cyclohexanedimethanol, 4-(2-hydroxyethyl)cyclohexanol and 2,2,4,4-tetramethyl-cyclobutane-1,3-diol;

glycols such as ethylene glycol, 2,2'-oxydiethanol (namely, diethylene glycol), triethylene glycol, propylene glycol and spiroglycol;

aralkyl diols such as 1,2-benzenedimethanol, 1,3-benzenedimethanol, 1,4-benzenedimethanol, 1,4-benzenediethanol, 1,3-bis(2-hydroxyethoxy)benzene, 1,4-bis(2-hydroxyethoxy)benzene, 2,3-bis(hydroxymethyl)naphthalene, 1,6-bis(hydroxyethoxy)naphthalene, 4,4'-biphenyldimethanol, 4,4'-biphenyldiethanol, 1,4-bis(2-hydroxyethoxy)biphenyl, bisphenol A bis(2-hydroxyethyl) ether and bisphenol S bis(2-hydroxyethyl) ether;

cyclic ethers such as 1,2-epoxyethane (namely, ethylene oxide), 1,2-epoxypropane (namely, propylene oxide), 1,2-epoxycyclopentane, 1,2-epoxycyclohexane, 1,4-epoxycyclohexane, 1-methyl-1,2-epoxycyclohexane, 2,3-epoxynorbornane and 1,3-epoxypropane; and oxygen-containing heterocyclic dihydroxy compounds such as isosorbide, isomannide and isoidide.

One kind of the other dihydroxy compounds as described above may be used alone, or two or more kinds thereof may be used in an arbitrary combination and at an arbitrary ratio.

<Molecular Weight of Polycarbonate Resin>

The polycarbonate resin according to the present invention preferably has a viscosity average molecular weight (Mv), which is a molecular weight determined in terms of solution viscosity, of from 5,000 to 100,000. It is preferred that the polycarbonate resin have a viscosity average molecular weight equal to or higher than the above described lower limit value, because the mechanical properties of the polycarbonate resin according to the present invention tends to improve. Further, it is preferred that the polycarbonate resin have a viscosity average molecular weight equal to or lower than the above described upper limit value, because the flowability of the polycarbonate resin according to the present invention tends to be sufficient. In view of the above, the viscosity average molecular weight (Mv) of the polycarbonate resin according to the present invention is more preferably 10,000 or more, still more preferably 12,000 or more, particularly preferably 13,000 or more, and most particularly preferably 14,000 or more. At the same time, the viscosity average molecular weight is more preferably 40,000 or less, still more preferably 30,000 or less, particularly preferably 28,000 or less, and most particularly preferably 24,000 or less.

To control the viscosity average molecular weight of the polycarbonate resin according to the present invention within the above described range, two or more kinds of polycarbonate resins having different viscosity average molecular weights may be used in mixture. In this case, polycarbonate resins having a viscosity average molecular weight outside the above described suitable range may be used in mixture, to control the viscosity average molecular weight (Mv) of the polycarbonate resin according to the present invention.

The viscosity average molecular weight (Mv) of the polycarbonate resin, as used herein, refers to a value obtained by determining the intrinsic viscosity (limiting viscosity) [η] (unit: dL/g) with an Ubbelohde viscometer at a temperature of 20° C., using methylene chloride as a solvent, and calculating Mv according to the Schnell's viscosity equation, namely, $\eta=1.23\times10^{-4} \text{Mv}^{0.83}$. The intrinsic viscosity (limiting viscosity) [η] as used herein refers to a value determined by measuring the specific viscosity [$\eta_{sp}$] at each solution concentration [C] (g/dL), and calculating η according to the following equation.

$$\eta = \lim_{c \to 0} \eta_{sp}/c \qquad \text{[Equation 1]}$$

<Amount of Terminal Hydroxyl Groups in Polycarbonate Resin>

The amount of terminal hydroxyl groups in the polycarbonate resin according to the present invention is not particularly limited. However, the amount of terminal hydroxyl groups is usually from 10 to 3,000 ppm, preferably from 20 ppm or more, more preferably from 50 ppm or more, and still more preferably from 200 ppm or more. At the same time, the amount of terminal hydroxyl groups is preferably 2,000 ppm or less, more preferably 1,500 ppm or less, and still more preferably 1,000 ppm or less. When the amount of terminal hydroxyl groups is adjusted within the above described range, it is possible to improve the color, thermal stability and moist heat stability of the polycarbonate resin according to the present invention.

The amount of terminal hydroxyl groups in the polycarbonate resin according to the present invention can be adjusted within the above described range by using an arbitrary known method. For example, in cases where the polycarbonate resin according to the present invention is produced by polycondensation through a transesterification reaction, the amount of terminal hydroxyl groups can be controlled within the above described range, by adjusting the mixing ratio of a carbonate ester and the dihydroxy compound(s), the degree of pressure reduction during the transesterification reaction, and/or the like.

Further, a more active method of adjusting the amount of terminal hydroxyl groups may be, for example, a method in which a chain terminating agent is separately added during the reaction. Examples of the chain terminating agent to be used at this time include monohydric phenols, monovalent carboxylic acids and carbonic acid diesters. One kind of these chain terminating agents may be used alone, or two or more kinds thereof may be used in an arbitrary combination and at an arbitrary ratio.

Further, in cases where the polycarbonate resin according to the present invention is produced by interfacial polymerization, the amount of terminal hydroxyl groups can be adjusted arbitrarily, by controlling the amount of a molecular weight regulator (chain terminating agent) to be incorporated.

The amount of terminal hydroxyl groups is represented as the mass of the terminal hydroxyl groups with respect to the mass of the polycarbonate resin, in ppm. The amount of terminal hydroxyl groups is measured by colorimetric quantification using a titanium tetrachloride/acetic acid method (the method described in Macromol. Chem. 88 215 (1965)). In the case of a polycarbonate resin copolymer composed of a plurality of dihydroxy compounds, the measurement is carried out by: mixing the corresponding dihydroxy compounds depending on the copolymerization ratio, to prepare resin samples, at least in three concentration levels; forming a calibration curve based on the data of the three or more samples; and then determining the amount of terminal hydroxyl groups of the polycarbonate resin copolymer. The measurement is carried out at a detection wavelength of 546 nm.

[Method of Producing Polycarbonate Resin]

The polycarbonate resin according to the present invention can be produced by a known technique, and the production method can be selected as appropriate without particular limitation. The polycarbonate resin according to the present invention can be produced by polycondensation of the polyhydric phenol compound according to the present invention, the other dihydroxy compound which is used as necessary, and a carbonate-forming compound. Specific examples of the other dihydroxy compound include the above described dihydroxy compounds.

Examples of the carbonate-forming compound include carbonyl halides and carbonate esters. One kind of these carbonate-forming compounds may be used alone, or two or more kinds thereof may be used in an arbitrary combination and at an arbitrary ratio.

Specific examples of the carbonyl halide include phosgene; and haloformates such as bischloroformates of dihydroxy compounds, and monochloroformates of dihydroxy compounds.

Specific examples of the carbonate ester include: dialkyl carbonates such as dimethyl carbonate, diethyl carbonate and di-t-butyl carbonate; and substituted and unsubstituted diaryl carbonates such as diphenyl carbonate (hereinafter, sometimes referred to as "DPC"), bis(4-methylphenyl) carbonate, bis(4-chlorophenyl) carbonate, bis(4-fluorophenyl) carbonate, bis(2-chlorophenyl) carbonate, bis(2,4-difluorophenyl) carbonate, bis(4-nitrophenyl) carbonate, bis(2-nitrophenyl) carbonate, bis(methylsalicylphenyl) carbonate and ditolyl carbonate. Among these, diphenyl carbonate is preferred.

These carbonate esters may be used alone, or as a mixture of two or more kinds thereof.

Further, a part of the above descried carbonate ester, preferably in an amount of 50% by mole or less, more preferably 30% by mole or less, may be substituted with a dicarboxylic acid or a dicarboxylic acid ester. Representative examples of the dicarboxylic acid or the dicarboxylic acid ester which can be used for the substitution include terephthalic acid, isophthalic acid, diphenyl terephthalate and diphenyl isophthalate. Substitution with such a dicarboxylic acid or dicarboxylic acid ester gives a polyester carbonate.

The polycarbonate resin according to the present invention can be produced by a conventionally known polymerization method, and the polymerization method is not particularly limited. Examples of the polymerization method include methods such as interfacial polymerization, melt transesterification, pyridine method, ring-opening polymerization of a cyclic carbonate compound, and solid phase transesterification of a prepolymer.

In particular, the polyhydric phenol compound according to the present invention is preferably produced by a method in which the polymerization is carried out in the presence of an alkaline catalyst, since the polyhydric phenol compound has an excellent alkali resistance. The method in which the polymerization is carried out in the presence of an alkaline catalyst is more preferably interfacial polymerization or melt transesterification, and still more preferably melt transesterification. By employing such a production method in the production of a polycarbonate resin using the polyhydric phenol compound according to the present invention, a polycarbonate resin having an excellent color can be produced with a good productivity.

Particularly suitable methods, among the above described methods, will now be specifically described.

<Interfacial Polymerization>

First, a description will be given regarding a case in which the polycarbonate resin according to the present invention is produced by interfacial polymerization. In the interfacial polymerization, a dihydroxy compound as a raw material is allowed to react with a carbonate-forming compound (preferably, phosgene) in the presence of an organic solvent which is inert in the reaction and an aqueous alkaline solution, while maintaining the pH to 9 or more, in general. Thereafter, interfacial polymerization is carried out in the presence of a polymerization catalyst, to obtain a polycarbonate resin. In the reaction system, a molecular weight regulator (chain terminating agent) may be allowed to be present, as necessary, and an antioxidant may be allowed to be present in order to prevent the oxidation of the dihydroxy compound.

The dihydroxy compound as a raw material and the carbonate-forming compound are the same as those described above. Among the carbonate-forming compounds, phosgene is preferably used, and the method in which phosgene is used is particularly referred to as the "phosgene method".

Examples of the organic solvent which is inert in the reaction include: chlorinated hydrocarbons such as dichloromethane, 1,2-dichloroethane, chloroform, monochlorobenzene and dichlorobenzene; and aromatic hydrocarbons such as benzene, toluene and xylene; but not particularly limited thereto. One kind of these organic solvents may be used alone, or two or more kinds thereof may be used in an arbitrary combination and at an arbitrary ratio.

Examples of the alkali compound to be contained in the aqueous alkaline solution include: alkali metal compounds such as sodium hydroxide, potassium hydroxide, lithium hydroxide and sodium hydrogen carbonate; and alkaline earth metal compounds, but not particularly limited thereto. Among these, sodium hydroxide and potassium hydroxide are preferred. One kind of these alkali compounds may be used alone, or two or more kinds thereof may be used in an arbitrary combination and at an arbitrary ratio.

The concentration of the alkali compound to be contained in the aqueous alkaline solution is not limited. However, the alkali compound is usually used in an amount of from 5 to 10% by mass, in order to control the pH of the aqueous alkaline solution during the reaction within the range of from 10 to 12. In the case of blowing in phosgene into the reaction mixture, for example, it is preferred that the molar ratio of the dihydroxy compound as a raw material and the alkali compound be adjusted usually to 1:1.9 or more, and particularly to 1:2.0 or more, and at the same time, usually to 1:3.2 or less, and particularly to 1:2.5 or less, so that the pH of the aqueous phase can be controlled within the range of from 10 to 12, and preferably from 10 to 11.

Examples of the polymerization catalyst include, but not particularly limited to: aliphatic tertiary amines such as trimethylamine, triethylamine, tributylamine, tripropylamine and trihexylamine; alicyclic tertiary amines such as N,N'-dimethylcyclohexylamine and N,N'-diethylcyclohexylamine; aromatic tertiary amines such as N,N'-dimethylaniline and N,N'-diethylaniline; quaternary ammonium salts such as trimethylbenzylammonium chloride, tetramethylammonium chloride and triethylbenzylammonium chloride; pyridine; guanine; and salts of guanidine. One kind of these polymerization catalysts may be used alone, or two or more kinds thereof may be used in an arbitrary combination and at an arbitrary ratio.

Examples of the molecular weight regulator include, but not particularly limited to: aromatic phenols containing a monovalent phenolic hydroxyl group; aliphatic alcohols such as methanol and butanol; mercaptan; and phthalic imide. Among these, an aromatic phenol is preferred. Specific examples of such aromatic phenols include: phenol, o-n-butylphenol, m-n-butylphenol, p-n-butylphenol, o-isobutylphenol, m-isobutylphenol, p-isobutylphenol, o-t-butylphenol, m-t-butylphenol, p-t-butylphenol, o-n-pentylphenol, m-n-pentylphenol, p-n-pentylphenol, o-n-hexylphenol, m-n-hexylphenol, p-n-hexylphenol, p-t-octylphenol, o-cyclohexylphenol, m-cyclohexylphenol, p-cyclohexylphenol, o-phenylphenol, m-phenylphenol, p-phenylphenol, o-n-nonylphenol, m-n-nonylphenol, p-n-nonylphenol, o-cumylphenol, m-cumylphenol, p-cumylphenol, o-naphthylphenol, m-naphthylphenol and p-naphthylphenol; 2,5-di-t-butylphenol; 2,4-di-t-butylphenol; 3,5-di-t-butylphenol; 2,5-dicumylphenol; 3,5-dicumylphenol; p-cresol, bromophenol, tribromophenol, and a monoalkylphenol having a linear or branched alkyl group having from 12 to 35 carbon atoms in average, at the ortho-, meta- or para-position; 9-(4-hydroxyphenyl)-9-(4-methoxyphenyl)fluorene; 9-(4-hydroxy-3-methylphenyl)-9-(4-methoxy-3-methylphenyl)fluorene; and 4-(1-adamantyl)phenol. Among these, p-t-butylphenol, p-phenylphenol and p-cumylphenol are preferably used. One kind of these molecular weight regulators may be used alone, or two or more kinds thereof may be used in an arbitrary combination and at an arbitrary ratio.

The amount of the molecular weight regulator to be used is, but not particularly limited to, usually 0.5 moles or more, and preferably 1 mole or more, and at the same time, usually 50 moles or less, and preferably 30 moles or less, with respect to 100 moles of the dihydroxy compound as a raw material. When the amount of the molecular weight regulator used is adjusted within the above described range, the thermal stability and hydrolysis resistance of the resulting polycarbonate resin can be improved.

In the reaction, the reaction substrates (reaction raw materials), reaction medium/media (organic solvent(s)), catalyst(s), additive(s), etc., may be mixed in an arbitrary order as long as a desired polycarbonate resin can be obtained, and an appropriate order may be set arbitrarily. In cases where phosgene is used as the carbonate-forming compound, for example, the molecular weight regulator can be mixed at an arbitrary time point, as long as it is after the reaction (phosgenation) of the dihydroxy compound as a raw material with phosgene, and before the start of the polymerization reaction.

The reaction temperature is usually from 0 to 40° C., but not particularly limited thereto. The reaction time is usually from several minutes (for example, 10 minutes) to several hours (for example, six hours), but not particularly limited thereto.

<Melt Transesterification>

Next, a description will be given regarding a case in which the polycarbonate resin according to the present invention is produced by melt transesterification.

In the melt transesterification, a transesterification reaction of a carbonate ester and a dihydroxy compound as a raw material is carried out.

The dihydroxy compound as a raw material, and the carbonate ester are the same as those described above, but it is preferred that diphenyl carbonate be used as the carbonate ester.

The ratio of the dihydroxy compound as a raw material and the carbonate ester (in cases where a part of the carbonate ester is substituted with the above described dicarboxylic acid or dicarboxylic acid ester, the dicarboxylic acid or dicarboxylic acid ester is included in the carbonate ester; the same shall apply hereinafter) is arbitrary, as long as a desired polycarbonate resin can be obtained. Such a carbonate ester is preferably used in excess with respect to the amount of the dihydroxy compound as a raw material, when polymerized with the dihydroxy compound. Specifically, the carbonate ester is preferably used in an amount of from 1.01 to 1.30 times (molar ratio), and more preferably from 1.02 to 1.20 times (molar ratio) the amount of dihydroxy compound. When the carbonate ester is used in too small an amount in molar ratio with respect to the dihydroxy compound, the amount of terminal hydroxyl groups in the resulting polycarbonate resin is increased, as a result of which the thermal stability of the resin tends to deteriorate. When the carbonate ester is used in too large an amount in molar ratio with respect to the dihydroxy compound, on the other hand, the reaction speed of the transesterification is decreased, possibly resulting in a difficulty to produce a polycarbonate resin having a desired molecular weight, and/or the residual amount of the carbonate ester in the resulting resin is increased, possibly causing odor during molding or in the resulting molded article.

In cases where the polycarbonate resin is produced by melt transesterification, a transesterification catalyst is usually used. The transesterification catalyst is not particularly limited, and any conventionally known transesterification catalyst can be used. For example, it is preferred to use an alkali metal compound and/or an alkaline earth metal compound, as the transesterification catalyst. Further, supplementarily, a basic compound such as a basic boron compound, a basic phosphorus compound, a basic ammonium compound or an amine compound may be used in combination. One kind of the transesterification catalyst may be used alone, or two or more kinds thereof may be used in an arbitrary combination and at an arbitrary ratio.

The melt transesterification is usually carried out at a reaction temperature of from 100 to 320° C., but not particularly limited thereto. Further, the reaction is usually carried out under a reduced pressure condition of 2 mmHg or less, but not particularly limited thereto. Specifically, the melt transesterification can be carried out by allowing a melt polycondensation reaction to proceed under the above described conditions, while removing by-products.

The reaction can be carried out by either a batch process or a continuous process. In the case of carrying out a reaction by the batch process, the reaction substrates, reaction medium/media, catalyst(s), additive(s), etc., to be used in the reaction may be mixed in an arbitrary order as long as a desired polycarbonate resin can be obtained, and an appropriate order may be set arbitrarily. It is preferred, however, the melt transesterification reaction is carried out by the continuous process, particularly in view of the stability and the like of the polycarbonate resin.

In the melt transesterification, a catalyst deactivating agent may be used as required. As the catalyst deactivating agent, a compound capable of neutralizing the transesterification catalyst can be arbitrarily used. Examples thereof include: sulfur-containing acidic compounds and derivatives thereof; and phosphorus-containing acidic compounds and derivatives thereof. One kind of these catalyst deactivating agents may be used alone, or two or more kinds thereof may be used in an arbitrary combination and at an arbitrary ratio.

The amount of the catalyst deactivating agent used is, but not particularly limited to, usually 0.5 equivalents or more, and preferably 1 equivalent or more, and at the same time, usually 20 equivalents or less, and preferably 10 equivalents or less, with respect to the amount of alkali metal or alkaline earth metal contained in the above described transesterification catalyst. Further, the amount of the catalyst deactivating agent used is usually 1 ppm or more, and at the same time, usually 100 ppm or less and preferably 50 ppm or less, with respect to the amount of the resulting polycarbonate resin.

EXAMPLES

Examples of the present invention will now be described below. However, the present invention is in no way limited to these Examples.

Various analysis methods used in the following Examples and Comparative Examples are as shown below.

<Proton Nuclear Magnetic Resonance (1H NMR) Analysis>

A quantity of 20 mg of a sample was dissolved in 0.5 ml of deuterated chloroform, and the resulting solution was analyzed by a nuclear magnetic resonance (NMR) apparatus, AVANCE 400, manufactured by Bruker.

<High Performance Liquid Chromatography-Mass Spectrometer (LC-MS) Analysis>

A quantity of 20 mg of a sample was dissolved in 100 ml of acetonitrile. The resulting solution was analyzed by a high performance liquid chromatography-mass spectrometer, Acquity, manufactured by Waters Corporation.

Measurement conditions are as shown below.

Column: UPLC BEH C18, particle size: 1.7 μm, 2.1×100 mm (manufactured by Waters Corporation)

Column temperature: 40° C.

Dissolution solvent: a 50% by mass tetrahydrofuran-acetonitrile solution (L1)/a 0.1% by mass aqueous solution of ammonium acetate (L2)

Detector: LCT Premier XE (manufactured by Waters Corporation)

Measurement mode: APCI (−)

Dissolution conditions (solvent ratio is shown in a volume ratio): 0.35 ml/min 0 to 18 min, L1:L2=60:40→99:1 (linear concentration change)

18 to 25 min, L1:L2=99:1

<Absorption Intensity Ratio at 254 nm>

A quantity of 20 mg each of the polyhydric phenol compounds obtained in Examples and Comparative Examples was dissolved in 100 ml of acetonitrile. A quantity of 5 μl of the resulting solution was then eluted using as an eluent a mixed liquid of acetonitrile and a 0.1% by mass aqueous solution of ammonium acetate. The measurement and analysis were carried out under the following conditions, to determine the areas of the peaks corresponding to the respective compounds, and the area ratio of the respective peaks was calculated.

(Measurement Conditions)

Controller: SCL-10AVP, manufactured by Shimadzu Corporation

Column: inertsil ODS3V (4.6×150 mm, 5 μm), manufactured by GL Sciences Inc.

Column oven: CTO-10AVP, manufactured by Shimadzu Corporation; 40° C.

Pump: LC-10ADVP, manufactured by Shimadzu Corporation; flow rate: 1.0 ml/min

Elution conditions: K1=acetonitrile, K2=a 0.1% by mass aqueous solution of ammonium acetate K1/K2=60/40 (0 to 5 minutes)

K1/K2=60/40→95/5 (linear concentration change, 5 to 30 minutes)

K1/K2=95/5 (30 to 80 minutes)

(ratio: volume ratio)

Detector: SPD-10AVP, manufactured by Shimadzu Corporation; UV 254 nm (Analysis Conditions)

Software: LC-solution ver. 1.22 SP1, manufactured by Shimadzu Corporation

Settings: Width=5, Slope=200, Drift=0, T. DBL=1,000, Min. Area=500

In cases where no peak was detected under the present analysis conditions, the corresponding peak was determined to be "below the detection limit".

The peaks to which the bisphenol compound (A) and the trisphenol compound (B) correspond were determined by isolating components corresponding to the respective peaks by silica gel column chromatography, and then identifying the peaks by the above described NMR or LC-MS analysis.

<Color when Dissolved in Alcohol>

Each of the polyhydric phenol compounds obtained in Examples and Comparative Examples was dissolved in ethanol (manufactured by Wako Pure Chemical Industries, Ltd.; purity: 99.5%), to prepare a 1 wt/vol % ethanol solution of each polyhydric phenol compound. Next, using a UV-visible spectrophotometer, Model "V-630" manufactured by JASCO Corporation, the absorbance of the above described ethanol solution of the polyhydric phenol compound was measured under the following conditions. The difference in absorbance between the measured values obtained at wavelengths of 410 nm and 500 nm, was determined as the value of "color when dissolved in alcohol". In Table 5, this is shown as the "color when dissolved in alcohol".

A lower value of the "color when dissolved in alcohol" indicates a lower degree of coloration (yellowing) of the polyhydric phenol compound itself, and thus is preferred.

Measured cell: a quartz cell having an optical path length of 50 mm

Scanning speed: 400 nm/min

Measurement range: from 380 to 600 nm

Baseline correction: ethanol (the same as that used in the preparation of the above described ethanol solution of the polyhydric phenol compound)

Response: FAST

<Color when Dissolved in Alkali>

A 25 wt/vol % aqueous solution of sodium hydroxide (manufactured by Wako Pure Chemical Industries, Ltd.) was diluted with pure water, to prepare a 1.5 mol/L aqueous solution of sodium hydroxide. Subsequently, 1.7 g of sodium hydrosulfite (a special grade reagent, manufactured by Wako Pure Chemical Industries, Ltd.) was added to 1 L of the thus prepared 1.5 mol/L aqueous solution of sodium hydroxide in order to eliminate the effect of oxygen, and dissolved with stirring, to prepare an aqueous solution of sodium hydroxide-sodium hydrosulfite. After heating the thus prepared aqueous solution of sodium hydroxide-sodium hydrosulfite to 35° C., each of the polyhydric phenol compounds obtained in the Examples and Comparative Examples was added to the solution, and dissolved by stirring for 15 minutes, to prepare a 0.167 wt/vol % aqueous solution of the polyhydric phenol compound-sodium hydroxide-sodium hydrosulfite. Next, the absorbance of the thus prepared aqueous solution of the polyhydric phenol compound-sodium hydroxide-sodium hydrosulfite was measured under the same conditions as those for the determination of the above described "color when dissolved in alcohol". It is to be noted, however, that the baseline correction was carried out using the above described aqueous solution of sodium hydroxide-sodium hydrosulfite. The difference in absorbance between the measured values obtained at wavelengths of 410 nm and 500 nm, was determined as the value of "color when dissolved in alkali". In Table 5, this is shown as the "color when dissolved in alkali".

A lower value of the "color when dissolved in alkali" indicates a lower degree of coloration (yellowing) of the alkaline solution of the polyhydric phenol compound, and thus is preferred.

<Alkali Stability>

In order to match the concentrations of the measured solutions, the value of the "color when dissolved in alkali" obtained as described above was multiplied by 6, which is a correction coefficient, and the difference between the thus obtained value and the value of the "color when dissolved in alcohol" was calculated as the alkali stability. The equation for calculating the alkali stability is as shown below. In Table 5, this is shown as the "Alkali stability".

A lower value of the alkali stability indicates a higher degree of coloring resistance (yellowing resistance) to alkali of the polyhydric phenol compound itself, and thus is preferred.

[Alkali stability]=[color when dissolved in alkali]×6−[color when dissolved in alcohol]

<Loss on Drying Analysis>

A quantity of 10 g of a wet sample containing a solvent was introduced into a 50 ml sample bottle, and dried at 40° C./20 Torr to adjust the solvent content to 15% by mass. Subsequently, the resultant was dried under reduced pressure at 60° C./20 Torr for six hours, and 5.0 g of the dried sample was subjected to melting and solvent removal at 120° C. and at normal pressure, in accordance with the method defined in JIS K0067 (1992). The solvent content of the resulting sample was determined from the change in the weight of the sample before and after the solvent removal treatment. Analysis was carried out on two lots of each sample, and the mean value of the thus determined solvent content was taken as the solvent content of each sample under the above described drying test conditions.

Example 1: Synthesis of Polyhydric Phenol Compound (Mixture Composed of Phenol Compounds (p-1-6), (p-2-6) and (q-6)) Containing 1,1-Bis(4-hydroxyphenyl)dodecane as Main Component Phenol (237 g) was heated to 40° C. and melted, and then concentrated hydrochloric acid (3.15 g) was added thereto. To the resulting mixture, a mixed liquid of dodecanal (92.0 g) and toluene (55.2 g) was added dropwise over four hours.

After the completion of the dropping, the mixture was matured at 40° C. for one hour. Thereafter, a 5% by mass aqueous solution of sodium hydrogen carbonate (55.9 g) was used to terminate the reaction, and 7.7% by mass of sodium dihydrogen phosphate (51.9 g) was added to the reaction mixture. Toluene, phenol and water were removed from the resulting reaction mixture by distillation under reduced pressure, and the resultant was extracted with toluene (405 g) and washed four times with water (230 g). Subsequently, the solvent was removed by distillation, to obtain a crude mixture containing phenol compounds (p-1-6), (p-2-6) and (q-6).

To the thus obtained crude mixture, 2-propanol (82.8 g) and heptane (460 g) were added, and the resultant was heated to an internal temperature of 70° C. to dissolve the mixture. Thereafter, the resultant was cooled to 52° C., and then seed crystals (50.0 mg) of 1,1-bis(4-hydroxyphenyl)dodecane were added thereto. After maturing for 30 minutes, the resultant was cooled to an internal temperature of 15° C. at a rate of 10° C./h, to complete the precipitation of powder. The resulting powder was filtered, and then dried under reduced pressure at 70° C. to obtain crude crystals. Toluene (330 g) and heptane (330 g) were added to the thus obtained crude crystals, and the resultant was heated to an internal temperature of 70° C. to dissolve the crystals. Subsequently, the resultant was cooled to 45° C., and then seed crystals (50.0 mg) of 1,1-bis(4-hydroxyphenyl)dodecane were added thereto. After maturing for 30 minutes, the resultant was cooled to an internal temperature of 15° C. at a rate of 10° C./h, to complete the precipitation of powder.

The resulting powder was filtered, and heptane (27.6 g) was sprinkled over the powder three times to carry out washing, followed by drying under reduced pressure at 70° C. to obtain a polyhydric phenol compound of interest, as a white solid (53.1 g).

The purity (absorption intensity ratio at 254 nm) of the bisphenol compounds (p-1-6) and (p-2-6), and the trisphenol compound (q-6), as well as the elution time of each of the components obtained by HPLC analysis were as shown below. The compound corresponding to the bisphenol compound (p-3-6) was below the detection limit.
<Purity>
(p-1-6):(p-2-6):(q-6)=99.94:0.06:0.09
<Elution Time>
(p-1-6): 26.0 min
(p-2-6): 27.5 min
(q-6): 44.0 min to 49.0 min Example 2: Synthesis of Polyhydric Phenol Compound (Mixture Composed of Phenol Compounds (p-1-6), (p-2-6) and (q-6)) Containing 1,1-Bis(4-hydroxyphenyl)dodecane as Main Component The same procedure as in Example 1 was repeated to obtain a crude mixture containing the phenol compounds (p-1-6), (p-2-6) and (q-6).

To the thus obtained crude mixture, 2-propanol (82.8 g) and heptane (460 g) were added, and the resultant was heated to an internal temperature of 70° C. to dissolve the mixture. Subsequently, the resultant was cooled to 52° C., and then seed crystals (50.0 mg) of 1,1-bis(4-hydroxyphenyl)dodecane were added thereto. After maturing for 30 minutes, the resultant was cooled to an internal temperature of 15° C. at a rate of 10° C./h, to complete the precipitation of powder. The resulting powder was filtered, and a mixed liquid of 2-propanol (4.14 g) and heptane (23.0 g) was sprinkled over the powder three times to carry out washing, followed by drying under reduced pressure at 70° C. to obtain a polyhydric phenol compound of interest, as a white solid (70.8 g).

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=99.80:0.20:0.21

Example 3: Synthesis of Polyhydric Phenol Compound (Mixture Composed of Phenol Compounds (p-1-5), (p-2-5) and (q-5)) Containing 1,1-Bis(4-hydroxyphenyl)undecane as Main Component The same procedure as in Example 1 was repeated except that undecanal (85.0 g) was used instead of dodecanal, to obtain a crude mixture containing phenol compounds (p-1-5), (p-2-5) and (q-5).

To the thus obtained crude mixture, toluene (330 g) and heptane (330 g) were added, and the resultant was heated to an internal temperature of 70° C. to dissolve the mixture. Thereafter, the resultant was cooled to an internal temperature of 15° C. at a rate of 10° C./h, to complete the precipitation of powder. The resulting powder was filtered, and then dried under reduced pressure at 70° C. to obtain crude crystals. Toluene (330 g) and heptane (330 g) were added to the thus obtained crude crystals, and the resultant was heated to an internal temperature of 70° C. to dissolve the crystals. Subsequently, the resultant was cooled to 38° C., and then seed crystals (50.0 mg) of 1,1-bis(4-hydroxyphenyl)undecane were added thereto. After maturing for 30 minutes, the resultant was cooled to an internal temperature of 15° C. at a rate of 10° C./h, to complete the precipitation of powder. The resulting powder was filtered, and heptane (27.6 g) was sprinkled over the powder three times to carry out washing, followed by drying under reduced pressure at 70° C. to obtain a polyhydric phenol compound of interest, as a white solid (57.8 g).

The purity (absorption intensity ratio at 254 nm) of the bisphenol compounds (p-1-5) and (p-2-5), and the trisphenol compound (q-5), as well as the elution time of each of the components obtained by HPLC analysis were as shown below. The compound corresponding to the bisphenol compound (p-3-5) was below the detection limit.
<Purity>
(p-1-5):(p-2-5):(q-5)=99.80:0.20:0.30
<Elution Time>
(p-1-5): 23.3 min
(p-2-5): 24.9 min
(q-5): 39.0 min to 46.0 min Example 4: Synthesis of Polyhydric Phenol Compound (Mixture Composed of Phenol Compounds (p-1-6), (p-2-6) and (q-6)) Containing 1,1-Bis(4-hydroxyphenyl)dodecane as Main Component The same procedure as in Example 1 was repeated to obtain a crude mixture containing the phenol compounds (p-1-6), (p-2-6) and (q-6).

Toluene (330 g) and heptane (330 g) were added to the thus obtained crude mixture, and the resultant was heated to an internal temperature of 70° C. to dissolve the mixture. Thereafter, the resultant was cooled to an internal temperature of 5° C. at a rate of 10° C./h, to complete the precipitation of powder. The resulting powder was filtered, and then dried under reduced pressure at 70° C. to obtain crude crystals. Toluene (69.0 g) and heptane (294 g) were added to the thus obtained crude crystals, and the resultant was heated to an internal temperature of 70° C. to dissolve the crystals. Subsequently, the resultant was cooled to 37° C., and then seed crystals (50.0 mg) of 1,1-bis(4-hydroxyphenyl)dodecane were added thereto. After maturing for 30 minutes, the resultant was cooled to an internal temperature of 15° C. at a rate of 10° C./h, to complete the precipitation of powder. The resulting powder was filtered, and then dried under reduced pressure at 70° C. to obtain crude crystals. A mixed liquid of toluene (368 g) and heptane (184 g) was added to the thus obtained crude crystals, and the resulting mixture was stirred at an internal temperature of 15° C. for one hour. The resulting mixed liquid was filtered, and heptane (27.6 g) was sprinkled over the powder three times to carry out washing, followed by drying under reduced pressure at 70° C. to obtain a polyhydric phenol compound of interest, as a white solid (49.6 g).

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=99.92:0.08:0.44

Example 5: Synthesis of Polyhydric Phenol Compound (Mixture Composed of Phenol Compounds (p-1-6), (p-2-6) and (q-6)) Containing 1,1-Bis(4-hydroxyphenyl)dodecane as Main Component The same procedure as in Example 1 was repeated to obtain a crude mixture containing the phenol compounds (p-1-6), (p-2-6) and (q-6).

To the thus obtained crude mixture, 2-propanol (46.0 g) and heptane (460 g) were added, and the resultant was heated to an internal temperature of 70° C. to dissolve the mixture. Thereafter, the resultant was cooled to 52° C., and then seed crystals (50.0 mg) of 1,1-bis(4-hydroxyphenyl)dodecane were added thereto. After maturing for 30 minutes, the resultant was cooled to an internal temperature of 15° C. at a rate of 10° C./h, to complete the precipitation of powder. The resulting powder was filtered, and 2-propanol (2.3 g) and heptane (23.0 g) were sprinkled over the powder three times to carry out washing, followed by drying under reduced pressure at 70° C. to obtain a polyhydric phenol compound of interest, as a white solid (72.6 g).

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=99.50:0.50:0.70

Example 6: Synthesis of Polyhydric Phenol Compound (Mixture Composed of Phenol Compounds (p-1-3), (p-2-3) and (q-3)) Containing 1,1-Bis(4-hydroxyphenyl)nonane as Main Component The same procedure as in Example 1 was repeated except that nonanal (71.0 g) was used instead of dodecanal, to obtain a crude mixture containing phenol compounds (p-1-3), (p-2-3) and (q-3).

To the thus obtained crude mixture, toluene (330 g) and heptane (330 g) were added, and the resultant was heated to an internal temperature of 70° C. to dissolve the mixture. Thereafter, the resultant was cooled to an internal temperature of 5° C. at a rate of 10° C./h, to complete the precipitation of powder. The resulting powder was filtered, and then dried under reduced pressure at 70° C. to obtain crude crystals. A mixed liquid of toluene (330 g) and heptane (330 g) was added to the thus obtained crude crystals, and the resulting mixture was stirred at an internal temperature of 15° C. for one hour. The resulting mixed liquid was filtered, and heptane (27.6 g) was sprinkled over the powder three times to carry out washing, followed by drying under reduced pressure at 70° C. to obtain a polyhydric phenol compound of interest, as a white solid (56.1 g).

The purity (absorption intensity ratio at 254 nm) of the bisphenol compounds (p-1-3) and (p-2-3), and the trisphenol compound (q-3), as well as the elution time of each of the components obtained by HPLC analysis were as shown below. The compound corresponding to the bisphenol compound (p-3-3) was below the detection limit.
<Purity>
(p-1-3):(p-2-3):(q-3)=99.90:0.10:1.00
<Elution Time>
(p-1-3): 17.0 min
(p-2-3): 18.8 min
(q-3): 31.0 min to 38.0 min Example 7: Synthesis of Polyhydric Phenol Compound (Mixture Composed of Phenol Compounds (p-1-6), (p-2-6) and (q-6)) Containing 1,1-Bis(4-hydroxyphenyl)dodecane as Main Component The same procedure as in Example 1 was repeated to obtain a crude mixture containing the phenol compounds (p-1-6), (p-2-6) and (q-6).

To the thus obtained crude mixture, toluene (330 g) and heptane (330 g) were added, and the resultant was heated to an internal temperature of 70° C. to dissolve the mixture. Thereafter, the resultant was cooled to an internal temperature of 5° C. at a rate of 10° C./h, to complete the precipitation of powder. The resulting powder was filtered, and then dried under reduced pressure at 70° C. to obtain crude crystals. A mixed liquid of toluene (330 g) and heptane (330 g) was added to the thus obtained crude crystals, and the resulting mixture was stirred at an internal temperature of 15° C. for one hour. The resulting mixed liquid was filtered, and then dried under reduced pressure at 70° C. to obtain a polyhydric phenol compound of interest, as a white solid (50.9 g).

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=99.50:0.50:1.23

Comparative Example 1: Synthesis of Polyhydric Phenol Compound (Mixture Composed of Phenol Compounds (p-1-6), (p-2-6) and (q-6)) Containing 1,1-Bis(4-hydroxyphenyl)dodecane as Main Component The same procedure as in Example 1 was repeated to obtain a crude mixture containing the phenol compounds (p-1-6), (p-2-6) and (q-6).

To the thus obtained crude mixture, methylene chloride (368 g) was added, and the resultant was heated to an internal temperature of 40° C. to dissolve the mixture. Thereafter, the resultant was cooled to an internal temperature of 5° C. at a rate of 10° C./h, to complete the precipitation of powder. The resulting powder was filtered, and then dried under reduced pressure at 70° C. to obtain crude crystals. Methylene chloride (368 g) was added to the thus obtained crude crystals, and the resultant was heated to an internal temperature of 40° C. to dissolve the crystals. Subsequently, the resultant was cooled to an internal temperature of 5° C. at a rate of 10° C./h, to complete the precipitation of powder. The resulting powder was filtered, and then methylene chloride (27.6 g) was sprinkled over the powder three times to carry out washing, followed by drying under reduced pressure at 70° C. to obtain a polyhydric phenol compound of interest, as a white solid (38.9 g).

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=98.50:1.50:1.60

Comparative Example 2: Synthesis of Polyhydric Phenol Compound (Mixture Composed of Phenol Compounds (p-1-6), (p-2-6) and (q-6)) Containing 1,1-Bis(4-hydroxyphenyl)dodecane as Main Component The same procedure as in Example 1 was repeated to obtain a crude mixture containing the phenol compounds (p-1-6), (p-2-6) and (q-6).

To the thus obtained crude mixture, toluene (330 g) and heptane (330 g) were added, and the resultant was heated to an internal temperature of 70° C. to dissolve the mixture. Thereafter, the resultant was cooled to an internal temperature of 5° C. at a rate of 10° C./h, to complete the precipitation of powder. The resulting powder was filtered, and then dried under reduced pressure at 70° C. to obtain crude crystals. Toluene (115 g) and heptane (230 g) were added to the thus obtained crude crystals, and the resultant was heated to an internal temperature of 70° C. to dissolve the crystals. Subsequently, the resultant was cooled to 37° C., and then seed crystals (50.0 mg) of 1,1-bis(4-hydroxyphenyl)dodecane were added thereto. After maturing for 30 minutes, the resultant was cooled to an internal temperature of 15° C. at a rate of 10° C./h, to complete the precipitation of powder. The resulting powder was filtered, and then dried under reduced pressure at 70° C. to obtain a polyhydric phenol compound of interest, as a white solid (45.1 g).

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=99.25:0.75:2.45

The contents of the bisphenol compound (a1), the bisphenol compound (a2) and the trisphenol compound (B) contained in each of the polyhydric phenol compounds obtained in the Examples and Comparative Examples described above, and the evaluation results of the respective polyhydric phenol compounds are shown in Table 5.

TABLE 5

|  |  | Example 1 | Example 2 | Example 3 | Example 4 | Example 5 | Example 6 | Example 7 | Comparative Example 1 | Comparative Example 2 |
|---|---|---|---|---|---|---|---|---|---|---|
| Bisphenol compound (a1) | Structural type | p-1-6 | p-1-6 | p-1-5 | p-1-6 | p-1-6 | p-1-3 | p-1-6 | p-1-6 | p-1-6 |
| Bisphenol compound (a2) |  | p-2-6 | p-2-6 | p-2-5 | p-2-6 | p-2-6 | p-2-3 | p-2-6 | p-2-6 | p-2-6 |
| Trisphenol compound (B) |  | q-6 | q-6 | q-5 | q-6 | q-6 | q-3 | q-6 | q-6 | q-6 |
| Bisphenol compound (a1) | Absorption intensity ratio at 254 nm (area ratio) | 99.94 | 99.80 | 99.80 | 99.92 | 99.50 | 99.90 | 99.50 | 98.50 | 99.25 |
| Bisphenol compound (a2) |  | 0.06 | 0.20 | 0.20 | 0.08 | 0.50 | 0.10 | 0.50 | 1.50 | 0.75 |
| Trisphenol compound (B) |  | 0.09 | 0.21 | 0.30 | 0.44 | 0.70 | 1.00 | 1.23 | 1.60 | 2.45 |
| Color when dissolved in alcohol |  | — | 0.0023 | 0.0033 | 0.0035 | 0.0022 | 0.0027 | 0.0029 | 0.0030 | 0.0032 | 0.0037 |
| Color when dissolved in alkali |  | — | 0.0445 | 0.0468 | 0.0488 | 0.0512 | 0.0520 | 0.0600 | 0.0646 | 0.0970 | 0.0952 |
| Alkali Stability |  | — | 0.2647 | 0.2775 | 0.2893 | 0.3050 | 0.3093 | 0.3571 | 0.3846 | 0.5788 | 0.5675 |

* Since the total of the values of the bisphenol compound (a1) and the bisphenol compound (a2) is "100", the value of the trisphenol compound (B) corresponds to the absorption intensity ratio at 254 nm (% by area) of the trisphenol compound (B) with respect to the bisphenol compound (A).

It is evident from the results shown in Table 5 that the polyhydric phenol compounds of the Examples, in each of which the amount of the trisphenol compound (B) was adjusted within the range defined in the present invention, have a markedly improved alkali stability, as compared to the polyhydric phenol compounds of the Comparative Examples, in each of which the amount of the trisphenol compound (B) is greater than the range defined in the present invention. In addition, it can be seen that adjusting the content of the bisphenol compound (a2) within the suitable range defined in the present invention also serves to improve the alkali stability.

Further, although no large differences in the "color when dissolved in alcohol" were observed between the polyhydric phenol compounds of Examples and those of Comparative Examples, there were differences in the "color when dissolved in alkali" therebetween. Therefore, it is also evident from the results that adjusting the amount of the trisphenol compound (B) within the range defined in the present invention serves to improve not the color of the polyhydric phenol compounds themselves, but the coloring resistance (yellowing) of the polyhydric phenol compounds when subjected to alkaline conditions.

The present invention has been made based on such a novel finding. It can be seen that the polyhydric phenol compound according to the present invention created based on such a finding is extremely useful, since the polyhydric phenol compound enables to produce a resin with little coloration when used as a raw material for a polycarbonate resin, a polyester resin or the like, which is polymerized under alkaline conditions, and allows for forming a polymer which can be formed into a molded product having an excellent alkali resistance.

Example 8: Synthesis of Solvent-Containing Product of Polyhydric Phenol Compound (Mixture Composed of Phenol Compounds (p-1-6), (p-2-6) and (q-6)) Containing 1,1-bis(4-hydroxyphenyl) dodecane as Main Component The precipitation step was carried out under the same conditions as those used in Example 2 to obtain a polyhydric phenol compound containing 2-propanol and heptane, as a white solid. Thereafter, heptane (20.0 g) was sprinkled over the surface of the resulting powder three times to carry out washing. The resultant was dried under reduced pressure at 40° C. to adjust the solvent content to 15% by mass, and a portion of the thus obtained white solid (83.2 g) was used in the above described drying test.

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=99.80:0.20:0.19

Comparative Example 3: Synthesis of 1,1-Bis(4-hydroxyphenyl)dodecane which Substantially does not Contain (p-2-6) and (q-6)

The precipitation step, the washing step, and the drying step under reduced pressure at 70° C. were carried out in the same manner as Example 2 to obtain a white solid (70.0 g). To the resulting white solid, 2-propanol (42.0 g) and heptane (210 g) were added, and the resultant was heated to an internal temperature of 70° C. to dissolve the solid. Thereafter, the resultant was cooled to 60° C., and then seed crystals (50.0 mg) of 1,1-bis(4-hydroxyphenyl)dodecane were added thereto. After maturing for 30 minutes, the resultant was cooled to an internal temperature of 15° C. at a rate of 10° C./h, to complete the precipitation of powder. The resulting powder was filtered, and a mixed liquid of 2-propanol (5.0 g) and heptane (25.0 g) was sprinkled over the powder three times to carry out washing, followed by washing with heptane (20 g) for three times, to obtain a polyhydric phenol compound containing solvents, as a white solid. The resultant was dried under reduced pressure at 40° C. to adjust the solvent content to 15% by mass, and a portion of the thus obtained white solid (83.2 g) was used in the above described drying test.

In the resulting bisphenol compound, compounds corresponding to the bisphenol compounds (p-2-6) and (p-3-6), and to the trisphenol compound (q-6) were below the detection limit.

Example 9: Synthesis of Solvent-Containing Product of Polyhydric Phenol Compound (Mixture Composed of Phenol Compounds (p-1-6), (p-2-6) and (q-6)) Containing 1,1-bis(4-hydroxyphenyl) dodecane as Main Component The same procedure as in Comparative Example 3 was repeated to obtain a powder (80.0 g) of the bisphenol compound (p-1-6) which does not substantially contain compounds corresponding to the bisphenol compounds (p-2-6) and (p-3-6), and to the trisphenol compound (q-6). To the thus obtained powder, a filtrate (70.0 g) obtained by carrying out the precipitation step in the same manner as in Example 2 was added, to obtain a mixture containing the bisphenol compounds (p-1-6) and (p-2-6), and the trisphenol compound (q-6). After removing the solvents by distillation under reduced pressure, the precipitation step was carried out in the same manner as in Comparative Example 3, to obtain a polyhydric phenol compound containing solvents, as a white solid. The resultant was dried under reduced pressure at 40° C. to adjust the solvent content to 15% by mass, and a portion of the thus obtained white solid (75.9 g) was used in the above described drying test.

The purity (absorption intensity ratio at 254 nm) of the bisphenol compounds (p-1-6) and (p-2-6), and the trisphenol compound (q-6) was as shown below. The compound corresponding to the bisphenol compound (p-3-6) was below the detection limit.
<Purity>
(p-1-6):(p-2-6):(q-6)=99.95:0.05:0.05

Example 10: Synthesis of Solvent-Containing Product of Polyhydric Phenol Compound (Mixture Composed of Phenol Compounds (p-1-6), (p-2-6) and (q-6)) Containing 1,1-bis(4-hydroxyphenyl) dodecane as Main Component The same procedure as in Comparative Example 3 was repeated to obtain a powder (80.0 g) of the bisphenol compound (p-1-6) which does not substantially contain compounds corresponding to the bisphenol compounds (p-2-6) and (p-3-6), and to the trisphenol compound (q-6). To the thus obtained powder, a filtrate (35.0 g) obtained by carrying out the precipitation step in the same manner as in Example 2 was added, to obtain a mixture containing the bisphenol compounds (p-1-6) and (p-2-6), and the trisphenol compound (q-6). After removing the solvents by distillation under reduced pressure, the precipitation step was carried out in the same manner as in Comparative Example 3, to obtain a polyhydric phenol compound containing solvents, as a white solid. The resultant was dried under reduced pressure at 40° C. to adjust the solvent content to 15% by mass, and a portion of the thus obtained white solid (75.5 g) was used in the above described drying test.

The purity (absorption intensity ratio at 254 nm) of the bisphenol compound (p-1-6) and the trisphenol compound (q-6) was as shown below. The compounds corresponding to the bisphenol compounds (p-2-6) and (p-3-6) were below the detection limit.
<Purity>
(p-1-6):(q-6)=100:0.03

The contents of the bisphenol compound (a1), the bisphenol compound (a2) and the trisphenol compound (B) contained in each of the polyhydric phenol compounds obtained in the Examples 8 to 10 and Comparative Example 3 described above, and the evaluation results of the loss on drying analysis of the respective polyhydric phenol compounds are shown in Table 6.

TABLE 6

|  |  | Example 8 | Example 9 | Example 10 | Comparative Example 3 |
|---|---|---|---|---|---|
| Bisphenol compound (a1) | Structural type | p-1-6 | p-1-6 | p-1-6 | p-1-6 |
| Bisphenol compound (a2) |  | p-2-6 | p-2-6 | p-2-6 | p-2-6 |
| Trisphenol compound (B) |  | q-6 | q-6 | q-6 | q-6 |
| Bisphenol compound (a1) | Absorption intensity | 99.80 | 99.95 | 100.00 | 100.00 |
| Bisphenol compound (a2) | ratio at 254 nm | 0.20 | 0.05 | 0.00 | 0.00 |
| Trisphenol compound (B) | (area ratio) | 0.19 | 0.05 | 0.03 | 0.00 |
| Solvent content after drying test | % by mass | 1.8 | 6.6 | 7.5 | 9.9 |

\* Since the total of the values of the bisphenol compound (a1) and the bisphenol compound (a2) is "100", the value of the trisphenol compound (B) corresponds to the absorption intensity ratio at 254 nm (8 by area) of the trisphenol compound (B) with respect to the bisphenol compound (A).

It is evident from the results shown in Table 6 that the polyhydric phenol compounds of Examples 8 to 10 have a lower solvent content after the drying test, and thus, a lower load in the solvent removal step, as compared to the polyhydric phenol compound of Comparative Example 3. Since each of the powders was precipitated in the same manner, washed in the same manner, and subjected to the drying test after having been adjusted to the same solvent content, it is evident that the reduction in the load in the solvent removal step in each of the Examples is not attributed to the precipitation and the washing steps, but as a result of an improvement in the powder properties of each powder due to containing a trace amount of the trisphenol compound (q-6). Further, the comparison between the results of Example 8 and those of Examples 9 and 10 reveals that the drying speed of the powder of Example 8 is greatly improved. Based on the above, it can be said that it is possible to markedly reduce the load in the solvent removal step, without carrying out special steps such as grinding or classification, by preparing the polyhydric phenol compound as a powder containing equal to or more than a certain amount of the trisphenol compound (q-6).

What is claimed is:

1. A mixture of polyhydric phenol compounds comprising:

a mixture of bisphenol compound (A) of Formula (1):

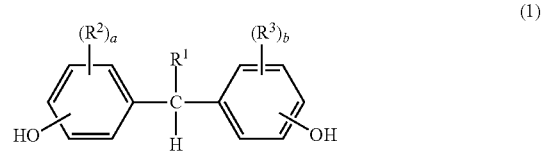

(1)

wherein in Formula (1), $R^1$ represents a monovalent aliphatic hydrocarbon group having from 6 to 24 carbon atoms; each of $R^2$ and $R^3$ independently represents a monovalent hydrocarbon group having from 1 to 15 carbon atoms; each of a and b are 0;
and
a mixture of trisphenol compound (B) of Formula (2):

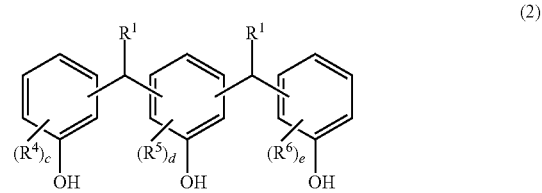

(2)

wherein in Formula (2), $R^1$ is the same as defined in the Formula (1); each of $R^4$, $R^5$ and $R^6$ independently represents a monovalent hydrocarbon group having from 1 to 15 carbon atoms; each of c, d and e are 0;

wherein the mixture of trisphenol compounds (B) is contained in a total amount, in terms of absorption intensity ratio at 254 nm, of 0.06% by area or more and less than 1.6% by area with respect to the total amount of the mixture of bisphenol compound (A).

2. The mixture of polyhydric phenol compounds according to claim 1, wherein the bisphenol compound (A) is a mixture of a bisphenol compound (a1) represented by the following Formula (3) and a bisphenol compound (a2) represented by the following Formula (4):

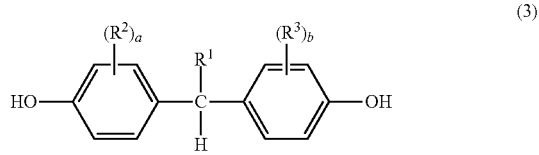
(3)

-continued

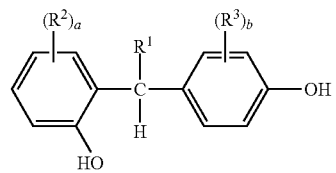
(4)

wherein in Formulae (3) and (4), $R^1$, $R^2$, $R^3$, a and b are the same as defined in the Formula (1), and wherein the ratio of the amount of the bisphenol compound (a2) with respect to the total amount of the bisphenol compound (a1) and the bisphenol compound (a2), in terms of absorption intensity ratio at 254 nm, is less than 1.5% by area.

3. The mixture of polyhydric phenol compounds according to claim 1, wherein $R^1$ has from 10 to 18 carbon atoms.

* * * * *